US011639334B2

(12) United States Patent
Muhuhi et al.

(10) Patent No.: US 11,639,334 B2
(45) Date of Patent: May 2, 2023

(54) METHODS FOR SYNTHESIS OF OXYPICOLINAMIDES

(71) Applicant: Corteva Agriscience LLC, Indianapolis, IN (US)

(72) Inventors: Joseck M. Muhuhi, Midland, MI (US); Megan A. Cismesia, Ann Arbor, MI (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

(21) Appl. No.: 17/275,640

(22) PCT Filed: Oct. 11, 2019

(86) PCT No.: PCT/US2019/055771
§ 371 (c)(1),
(2) Date: Mar. 11, 2021

(87) PCT Pub. No.: WO2020/081382
PCT Pub. Date: Apr. 23, 2020

(65) Prior Publication Data
US 2022/0041555 A1 Feb. 10, 2022

Related U.S. Application Data

(60) Provisional application No. 62/745,684, filed on Oct. 15, 2018.

(51) Int. Cl.
*C07D 213/81* (2006.01)
(52) U.S. Cl.
CPC .................................. *C07D 213/81* (2013.01)
(58) Field of Classification Search
CPC ................................................... C07D 213/81
See application file for complete search history.

(56) References Cited

U.S. PATENT DOCUMENTS

| | | | |
|---|---|---|---|
| 4,051,173 A | 9/1977 | Schacht | |
| 4,588,735 A | 5/1986 | Spalz | |
| 5,342,835 A | 8/1994 | Pepin et al. | |
| 5,401,871 A | 3/1995 | Talley | |
| 5,475,132 A | 12/1995 | Pepin et al. | |
| 5,563,165 A | 10/1996 | Talley | |
| 5,665,351 A | 9/1997 | Nair et al. | |
| 5,760,068 A | 6/1998 | Talley et al. | |
| 5,852,042 A | 12/1998 | Jakobi | |
| 6,355,660 B1 | 3/2002 | Ricks | |
| 6,410,572 B1 | 6/2002 | Schelberger | |
| 6,436,421 B1 | 8/2002 | Schindler | |
| 6,521,622 B1 | 2/2003 | Ricks | |
| 6,706,740 B2 | 3/2004 | Ricks | |
| 6,812,237 B2 | 11/2004 | Cowen et al. | |
| 6,812,238 B1 | 11/2004 | Fukuda et al. | |
| 6,861,390 B2 | 3/2005 | Meyer | |
| 6,903,219 B2 | 6/2005 | Niyaz | |
| 6,916,932 B2 | 7/2005 | Meyer | |
| 6,927,225 B2 | 8/2005 | Ricks | |
| 6,953,807 B2 | 10/2005 | Hutin et al. | |
| 7,034,035 B2 | 4/2006 | Ricks | |
| 7,183,278 B1 | 2/2007 | Imamura | |
| 7,241,804 B1 | 7/2007 | Hockenberry | |
| 7,250,389 B1 | 7/2007 | Sakanaka | |
| RE39,991 E | 1/2008 | Ricks | |
| 7,442,672 B2 | 10/2008 | Muller | |
| 7,459,581 B2 | 12/2008 | Derrer | |
| 7,560,565 B2 | 7/2009 | Bacque | |
| 7,927,617 B2 | 4/2011 | Koltzenburg | |
| 8,008,231 B2 | 8/2011 | Leatherman | |
| 8,153,819 B2 | 4/2012 | Dietz | |
| 8,236,962 B2 | 8/2012 | Hoekstra | |
| 8,349,877 B2 | 1/2013 | Brix | |
| 8,415,274 B2 | 4/2013 | Wachendorff-Neumann et al. | |
| 8,465,562 B2 | 6/2013 | Chen | |
| 8,470,840 B2 | 6/2013 | Klittich | |
| 8,476,193 B2 | 7/2013 | Keeney | |
| 8,580,959 B2 | 11/2013 | Devasthale | |
| 8,586,550 B2 | 11/2013 | Lee et al. | |
| 8,604,215 B2 | 12/2013 | Phiasivongsa | |
| 8,785,479 B2 | 7/2014 | Meyer | |
| 8,835,462 B2 | 9/2014 | Meyer | |
| 8,883,811 B2 | 11/2014 | Owen | |
| 8,916,579 B2 | 12/2014 | Boebel | |
| 9,006,259 B2 | 4/2015 | Boebel | |
| 9,084,418 B2 | 7/2015 | Ehr | |
| 9,131,690 B2 | 9/2015 | Meyer | |

(Continued)

FOREIGN PATENT DOCUMENTS

| CL | 2015001862 | 10/2015 |
|---|---|---|
| CN | 101530104 | 9/2009 |

(Continued)

OTHER PUBLICATIONS

Anonymous, Synergistic Fungicidal Composition of Heterocyclic Aromatic Amides and Triazoles, ip.com Journal, ip.com, Electronic Publication, West Henrietta, NY, US, Jul. 2004, 11 pages.
Backman, P., Fungicide Formulation: Relationship to Biological Activity, Ann. Rev. Phytopathol, 1978, 16, pp. 211-237.
BASF New Fungicide Xemium Got Full Approval in EU, Agronews, Jul. 18, 2012 [retrieved on Feb. 4, 2014]. Retrieved from the Internet: ,URL:http://news.agropages.com/News/NewsDetail---7386.htm, 1 page.
Bolton, M et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.
Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-855.
Cantacuzene, D., "Optimization of the papain catalyzed esterification of amino acids by alcohols and diols," Tetrahedron 45, 3 (1989): 741-748.

(Continued)

*Primary Examiner* — Timothy R Rozof

(57) ABSTRACT

The present technology relates to processes, mixtures and intermediates useful for making fungicide, florylpicoxamid. Also disclosed herein are processes for addition reactions which suppress epimerization and/or racemization.

11 Claims, No Drawings

(56) References Cited

U.S. PATENT DOCUMENTS

| | | |
|---|---|---|
| 9,144,239 B2 | 9/2015 | Meyer |
| 9,155,305 B2 | 10/2015 | Gary |
| 9,156,816 B2 | 10/2015 | Ito |
| 9,179,674 B2 | 11/2015 | Martin |
| 9,185,911 B2 | 11/2015 | Inami |
| 9,198,419 B2 | 12/2015 | Owen |
| 9,247,741 B2 | 2/2016 | DeLorbe |
| 9,265,253 B2 | 2/2016 | Li |
| 9,265,255 B2 | 2/2016 | Funke |
| 9,271,496 B2 | 3/2016 | Kemmitt |
| 9,271,497 B2 | 3/2016 | Lorsbach |
| 9,414,596 B2 | 8/2016 | Hoekstra et al. |
| 9,439,422 B2 | 9/2016 | Martin |
| 9,482,661 B2 | 11/2016 | Ross |
| 9,549,555 B2 | 1/2017 | DeLorbe |
| 9,549,556 B2 | 1/2017 | DeKorver |
| 9,629,365 B2 | 4/2017 | Li |
| 9,681,664 B2 | 6/2017 | Lalonde |
| 9,686,984 B2 | 6/2017 | DeKorver |
| 9,700,047 B2 | 7/2017 | Lu |
| 9,750,248 B2 | 9/2017 | Ouimette |
| 9,828,408 B2 | 11/2017 | Kalayanov et al. |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,301 B2 | 5/2018 | Quiroz et al. |
| 9,974,304 B2 | 5/2018 | DeKorver |
| 10,015,964 B2 | 7/2018 | Ogawa et al. |
| 10,015,966 B2 | 7/2018 | Taggi et al. |
| 10,111,432 B2 | 10/2018 | Rigoli |
| 10,172,354 B2 | 1/2019 | Ouimette et al. |
| 10,173,971 B2 | 1/2019 | Yao |
| 10,173,981 B2 | 1/2019 | Buchan |
| 10,182,568 B2 | 1/2019 | Bravo-Altamirano |
| 10,188,109 B2 | 1/2019 | Yao |
| 10,252,989 B2 | 4/2019 | Yao |
| 10,433,555 B2 | 10/2019 | Bravo-Altamirano et al. |
| 2002/0119979 A1 | 8/2002 | Degenhardt |
| 2002/0177578 A1 | 11/2002 | Ricks |
| 2003/0018052 A1 | 1/2003 | Ricks |
| 2003/0022902 A1 | 1/2003 | Ricks |
| 2003/0022903 A1 | 1/2003 | Ricks |
| 2005/0239873 A1 | 10/2005 | Hockenberry |
| 2006/0167281 A1 | 7/2006 | Meijer |
| 2007/0010401 A1 | 1/2007 | Noon |
| 2007/0066629 A1 | 3/2007 | Tormo i Blasco |
| 2009/0203770 A1 | 8/2009 | Hockenberry |
| 2009/0306142 A1 | 12/2009 | Carson |
| 2010/0016163 A1 | 1/2010 | Keiper |
| 2011/0070278 A1 | 3/2011 | Lopez |
| 2011/0082162 A1 | 4/2011 | Lorsbach |
| 2012/0245031 A1 | 9/2012 | Gewehr |
| 2013/0296372 A1 | 11/2013 | Owen |
| 2014/0051678 A1 | 2/2014 | Clement-Schatlo |
| 2014/0357713 A1 | 12/2014 | Damaj |
| 2015/0289508 A1 | 10/2015 | Meyer |
| 2015/0322051 A1 | 11/2015 | Lu |
| 2016/0037774 A1 | 2/2016 | Schulz |
| 2016/0183526 A1 | 6/2016 | Hopkins |
| 2016/0183527 A1 | 6/2016 | Hopkins |
| 2017/0183324 A1 | 6/2017 | Li |
| 2017/0273303 A1 | 9/2017 | DeKorver |
| 2017/0273306 A1 | 9/2017 | Lalonde |
| 2017/0290333 A1 | 10/2017 | Bravo-Altamirano |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |
| 2018/0002320 A1 | 1/2018 | Wilmot |
| 2018/0009755 A1* | 1/2018 | Whiteker ............. C07C 271/22 |

FOREIGN PATENT DOCUMENTS

| | | |
|---|---|---|
| FR | 2649699 | 1/1991 |
| JP | 19940026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 199741103 | 6/1997 |
| WO | 1997019908 | 6/1997 |
| WO | 1998018751 | 5/1998 |
| WO | 1999011127 | 11/1999 |
| WO | 2000076979 | 12/2000 |
| WO | 200114339 | 3/2001 |
| WO | 2005121069 | 12/2005 |
| WO | 2008079387 | 7/2008 |
| WO | 2012020777 | 8/2011 |
| WO | 2012016989 | 2/2012 |
| WO | 2016109301 | 12/2012 |
| WO | 2013136275 A1 | 9/2013 |
| WO | 2016007525 | 7/2015 |
| WO | 2016109288 | 12/2015 |
| WO | 2016109289 | 12/2015 |
| WO | 2016109290 | 12/2015 |
| WO | 2016109291 | 12/2015 |
| WO | 2016109300 | 12/2015 |
| WO | 2016109302 | 12/2015 |
| WO | 2016109303 | 12/2015 |
| WO | 2016109304 | 12/2015 |
| WO | 2016109305 | 12/2015 |
| WO | 2016106138 A1 | 6/2016 |
| WO | 2016122802 A1 | 8/2016 |
| WO | 2015005355 | 3/2017 |

OTHER PUBLICATIONS

FRAC Code List: Fungicides Sorted by Mode of Action (including FRAC Code numbering), Fungicide Resistance Action Committee, Dec. 2008, 10 pages.
Fungicidal Mixtures, IP.com Prior Art Database Technical Disclosure, (Jul. 5, 2005), XP055073888, DOI: http://ip.com/pdf/ipcompad/IPCOM000126160D.pdf, 12 pages.
Gisi, U., "Synergistic Interaction of Fungicides in Mixtures," The American Phytopathology Society, vol. 86, No. 11, 1996, pp. 1273-1279.
Guseynov et al: "Study of the reaction of aminoacetic acid with dihydric alcohols and production of epoxy esters" Chemical Problems, 2009 (1), pp. 188-190.
Hu, Z. et al., "Synthesis of Novel Analogues of Antimycin A3," Tetrahedron Letters 49 (2008), pp. 5192-5195.
Huang, C. et al., "Synergistic Interactions between Chitinase ChiCW and Fungicides Against Plant Fungal Pathogens," J. Microbiol. Biotechnol., 2008, 18(4), pp. 784-787.
Kissling, E., "Crop Protection Pipeline Value Jumps to Euro 2.4 Billion," BASF SE, Mar. 10, 2011 [retrieved on Feb. 4, 2014], Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D et al., ACS Symposium Series; American Chemical Society: Washington, D.C., 1995, pp. 15-24.
Latin, R., et al., "Re-Examining Fungicide Synergism for Dollar Spot Control," GCM, Juky 2008, pp. 84-87.
Ueki, M., et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-34.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.

(56) References Cited

OTHER PUBLICATIONS

PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 6 pages.
Tani, K. et al., "UK2A, B, C, and D, Novel Antifungal Antibiotics—from Streptomyces sp. 517-02.," The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from Streptomyces sp. 517-02," Bioorganic & Medicinal Chemistry Letters, vol. 15, No. 8, 2005, pp. 2011-2014.
Usuki, Y. et al., "UK-2A, B, C, and D, Novel Antifungal Antibiotics from Streptomyces sp. 517-02 VI (2). Structure-activity Relationships of UK-2A," Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Goellner et al. "Phakopsora pachyrhizi, the causal agent of Asian soybean rust." Molecular Plant Pathology, vol. 11, No. 2, pp. 169-177 (2010).
Fujita T, Ed. "Quantitative structure-activity analysis and database-aided bioisosteric structural transformation procedure as methodologies of agrochemical design"; Classical and Three Dimensional QSAR in Agrochemistry, ACS Symposium Series Washington, D.C. vol. 606, pp. 13-34 (1995).
Patani et al. Biosterism: A rational approach in drug design. Chemical Reviews, vol. 96, No. 8, pp. 3147-3176 (1996).
Kendall, S. et al. "Changes in sensitivity to DMI fungicides in Rhynchosporium secalis". Crop Protection, vol. 12, No. 5, pp. 357-362 (1993).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Shimano et al. "Total synthesis of the antifungal dilactones UK-2A and UK-3a: The determination of their relative and absolute configurations, analog synthesis and antifungal activities". Tetrahedron, vol. 54, pp. 12745-12774 (1998).
Lippard, S. "Chemical Synthesis: The Art of Chemistry". Nature, vol. 416, p. 587 (2002).

Washburn, W.N., "Identification of a nonbasic melanin hormone receptor 1 antagonist as an antiobesity clinical candidate." Journal of medicinal chemistry 57, 18 (Aug. 28, 2014): 7509-7522.
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012).
Chitwood, D. "Nematicides". Encyclopedia of Agrochemicals (3), pp. 1104-1115, John Wiley & Sons, New York, NY, http://naldc.nal.usda.gov/download/43874/PDF (2003).
Hanafi et al. "UK2A, B, C, and D, Novel Antifungal Antibiotics from Streptomyces sp 517-02 II. Structural Elucidation." The Journal of Antibiotics, vol. 49, Issue 12, pp. 1226-1231 (1996).
Shibata et al. "UK1, A Novel Cytotoxic Metabolite from Streptomyces sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Stephenson, G., et al. "Glossary of terms relating to pesticides". Pure and Applied Chemistry, vol. 78, No. 11, pp. 2075-2154, International Union of Pure and Applied Chemistry (2006).
Ueki, M., et al., "UK-1, A Novel Cytotoxic Metabolite from Streptomyces sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, A Novel Antifungal Antibiotic from Streptomyces sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from Streptomyces sp. 517-02". The Journal of Antibiotics, vol. 50, Issue 12, pp. 1052-1057 (1997).
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.
International Searching Authority, International Search Report and Written Opinion for PCT/US2019/021263 dated May 10, 2019, 15 pages.
International Searching Authority, International Search Report and Written Opinion for PCT/US18/030561 dated Jun. 27, 2019, 5 pages.

* cited by examiner

METHODS FOR SYNTHESIS OF OXYPICOLINAMIDES

1. CROSS-REFERENCE TO RELATED APPLICATIONS

This is a national phase entry under 35 U.S.C § 371 of international patent application PCT/US19/55771, filed on Oct. 11, 2019 and published in English as international patent publication WO 2020/081382, which claims priority to the benefit of U.S. Provisional Patent Application Ser. No. 62/745,684 filed Oct. 15, 2018, the disclosure of which is hereby incorporated by reference in its entirety.

2. BACKGROUND

Particular small molecules of the 4-methoxy-3-(acetyl or acetyloxymethyl) oxypicolinamide persuasion are of interest as being ascomycete fungi inhibitors and may be useful as fungicides for agricultural uses. Chiral compounds such as these oxypicolinamides can often be a challenge to manufacture on an industrial scale because of problems relating to intermediates and final product: yield; atom economy; and impurities. Moreover, the costs involved in multi-step syntheses at scale may significantly increase costs for each additional step required. Thus, operationally simple and limited-step processes to manufacture biologically active compounds at scale are highly desirable.

The syntheses of florylpicoxamid and applicable intermediates thereof currently employ addition reactions to carbonyl moieties. Such reactions often produce racemic and/or diastereomeric mixtures of chiral compounds. These impurities usually need to be separated in order to advance and characterize the final product, the active biological ingredient (ABI). Current synthetic methods of producing florylpicoxamid require a high loading of organic base. As such, synthetic intermediates and the final ABI are relatively impure upon immediate isolation from this reaction mixture and require purification by advanced methods, e.g. high performance liquid chromatography (HPLC).

Accordingly, there is a need in the field for better processes to synthesize chiral, diastereomeric compounds, especially those at scale. Such processes are advantageous in that they will improve the active's impurity profile, lower commercial manufacturing costs and improve efficiency and atom economy.

3. SUMMARY

The structure of florylpicoxamid is:

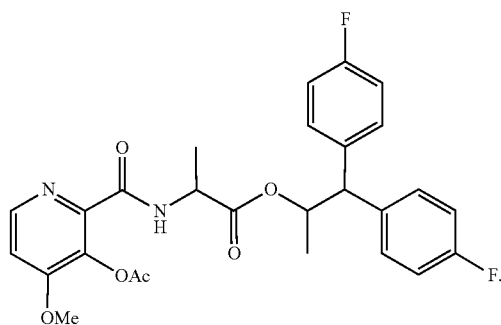 [SMILES: COc1ccnc(C(=O)NC(C)C(=O)OC(C)C(c2ccc(F)cc2)c2ccc(F)cc2)c1OC(C)=O]

Florylpicoxamid, CAS No. 1961312-55-9, is also known by its IUPAC name: (1)-2,2-bis(4-fluorophenyl)-1-methyl-ethyl N-{[3-(acetyloxy)-4-methoxy-2-pyridyl]carbonyl}-L-alaninate or by its chemical name: 1,1-bis(4-fluorophenyl)-propan-2-yl 2-(3-acetoxy-4-methoxypicolinamido) propanoate. In a more refined aspect, the disclosure provides for enantiomerically and/or diastereomerically enriched florylpicoxamid where the exact structure is:

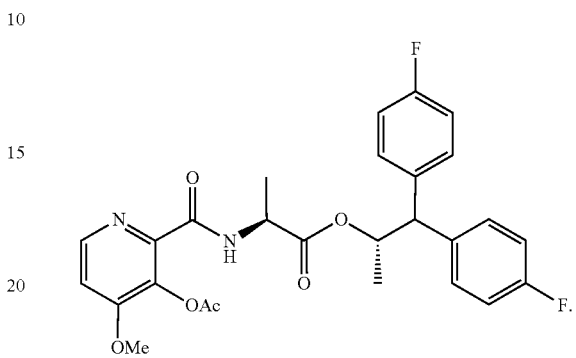

The synthesis of florylpicoxamid is described (Example 1a) in U.S. Pat. Nos. 10,040,764 and 10,035,772, each of which is hereby explicitly incorporated by reference in its entirety.

In one aspect, enantiomeric and/or diastereomeric enriched compounds or mixtures are provided. In some aspects, processes that make enantiomeric and/or diastereomeric enriched florylpicoxamid and intermediates thereof are provided.

In some aspects, compounds or mixtures disclosed herein are enantiomeric and/or diastereomeric enriched synthetic intermediates of florylpicoxamid and/or are protected forms or intermediates of florylpicoxamid; that is the compound is masked with a protecting organic functional group that when exposed to the appropriate conditions will cleave the chemical bond from the protecting group to produce florylpicoxamid.

In a further aspects, the processes described herein make a compound that is an ABI. In further aspects, mixtures are made that comprise a high percentage of enantiomeric and/or diastereomeric enriched florylpicoxamid or intermediates thereof. In some aspects, the processes described herein provide very low concentrations of undesired enantiomeric and/or diastereomeric compounds. These organic compounds are impurities, i.e. side-products from addition reactions and/or are cumulative, meaning these compounds (impurities) are present because one or more impure intermediates were carried forward in steps for the total synthesis of the ABI.

In one aspect, the processes described herein provide a total synthesis for making enantiomeric and/or diastereomeric enriched florylpicoxamid. In some aspects, the disclosure provides enantiomeric and/or diastereomeric enriched protected forms of florylpicoxamid or intermediates thereof.

In some aspects, mixtures comprising one or more compounds or salts thereof disclosed herein are provided.

In some aspects, a kit comprising one or more compounds disclosed herein, or one or more mixtures as disclosed herein, and optionally, instructions for use, is provided.

In various embodiments, the disclosure herein provides a compound that is selected from among certain specific compounds disclosed herein. In some aspects, the compound is any one of the compounds that is reduced to practice in the Examples section of this disclosure. In various aspects, the disclosure herein provides a compound that is selected such that the compound is within a genus formula disclosed herein.

In a still further aspect, methods of manufacture are provided.

4. DESCRIPTION

4.1. Definitions

Various terms used in the specification and claims herein are defined as set forth below, unless otherwise specifically defined in this disclosure. All technical and scientific terms not defined herein have the meaning commonly understood by a person skilled in the art to which this invention belongs.

"enantiomeric and/or diastereomeric enriched" refers to the amount (mol %) of a particular desired compound in a mixture of organic compounds disclosed herein. The other, undesired organic compounds in the mixture may be the enantiomer or the diastereomer of the desired compound, and as such these enantiomers and/or diastereomers are impurities. Otherwise, the impurity or impurities may be any one or more of the organic compounds disclosed herein.

"Substantially pure or free" refers to a mixture in which one organic compound of interest far exceeds the amount of other small organic compounds in the mixture as impurities, and is at least 95%, at least 96%, at least 97%, at least 98%, at least 99%, at least 99.5%, at least 99.7%, at least 99.9%, by mol, of the desired compound.

"Pg or protecting group" refers to any organic functional group which is a mask or as is traditional known in the art, is a group that "protects" a certain organic functional group with the ability to form that certain functional group upon bond cleavage. Examples include, but are not limited to: TMS, TBDMS, TBDPS, Ms, Ns, Tf, Fmoc, Boc, Cbz, Troc, Alloc, acetyl

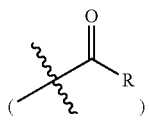

including acetamide where R=methyl or trifluoroacetamide where R=trifluouromethyl, hydroxylamine

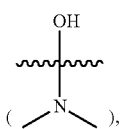

Tr or trityl (—C(Ph)$_3$), benzylidene

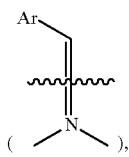

hydrazinyl

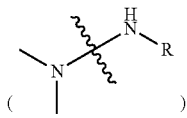

where R also can be C(O)R', benzoyl (—C(O)Ph), benzyl (—CH$_2$Ph), allyl, vinyl, Bu$^t$, and Piv. These groups, generally, are trivial to put on and there are many primary references in the literature to follow for the synthesis techniques, including the Wutz reference disclosed herein, which can assist the skilled artisan if they should need troubleshooting. Also, the skilled artisan will note that the groups referenced herein as "R" are a variety of organic functional groups that are selected from the group consisting of: alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

As used herein, the term "salt" refers to salts which are suitable for use in agriculture, i.e. they affect humans and lower animals without undue toxicity, irritation, allergic response and the like, and are commensurate with a reasonable benefit/risk ratio in agriculture. These salts are well known in the art. Salts of the compounds described herein include those derived from suitable inorganic and organic acids and bases. Examples of acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). $C_x$ alkyl refers to an alkyl group having x number of carbon atoms.

"Alkenyl" refers to straight or branched hydrocarbyl groups having from 1 to 6 carbon atoms and preferably 2 to 4 carbon atoms and having at least 1 and preferably from 1 to 2 sites of unsaturation (>C=C<). Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

In some embodiments, the substituted alkyl groups include halogenated alkyl groups and particularly halogenated methyl groups such as trifluoromethyl, difluromethyl, fluoromethyl and the like.

"Alkyl aryl" refers to an alkyl group having from 1 to 8, preferably 1 to 5, or more preferably 1 to 3 carbon atoms in length and is substituted specifically at any one of the carbons along the chain with an aryl group. "Alkenyl aryl" refers to an alkenyl or alkene group having from 1 to 8, preferably 1 to 5, or more preferably 1 to 3 carbon atoms in length and is substituted specifically at any one of the carbons along the chain with an aryl group. The aryl group can include heteroatoms or not. Alkynyl aryl" refers to an alkynyl or alkyne group having from 1 to 8, preferably 1 to 5, or more preferably 1 to 3 carbon atoms in length and is substituted specifically at any one of the carbons along the chain with an aryl group. The aryl group can include heteroatoms or not.

"Cycloalkyl" or "Cyclyl alkyl" refers to a saturated or partially saturated, but not aromatic, group having from 3 to 10 ring carbon atoms and no heteroatoms. Cycloalkyl encompasses single ring systems.

"Substituted alkenyl" refers to alkenyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Ar" and/or "aryl" refers to any group which is aromatic. This group must be cyclic; and does not contain heteroatoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{30}C(O)$alkyl, —$NR^{30}C(O)$substituted alkyl, —$NR^{30}C(O)$cycloalkyl, —$NR^{30}C(O)$ substituted cycloalkyl, —N $R^{30}C(O)$alkenyl, —$NR^{30}C(O)$ substituted alkenyl, alkoxy, substituted alkoxy-$NR^{30}C(O)$alkynyl, —$NR^{30}C(O)$substituted alkynyl, —$NR^{30}C(O)$aryl, —$NR^{30}C(O)$substituted aryl, —$NR^{30}C(O)$heteroaryl, —$NR^{30}C(O)$substituted heteroaryl, —$NR^{30}C(O)$heterocyclic, and —$NR^{30}C(O)$substituted heterocyclic wherein $R^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the groups H—C(N)—, alkyl-C(N)—, substituted alkyl-C(N)—, alkenyl-C(N)—, substituted alkenyl-C(N)—, alkynyl-C(N)—, substituted alkynyl-C(N)—, cycloalkyl-C(N)—, substituted cycloalkyl-C(N)—, aryl-C(N)—, substituted aryl-C(N)—, heteroaryl-C(N)—, substituted heteroaryl-C(N)—, heterocyclic-C(N)—, and substituted heterocyclic-C(N)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —$C(O)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl carbonyloxy" refers to the group —$C(NR^{33})OR^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —$C(S)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{30}C(O)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —$NR^{30}C(S)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where $R^{33}$, $R^{34}$, and $R^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminosulfonylamino, aminocarbonyloxy, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, a monosaccharide (which may be covalently bonded to the aryl group thru any oxygen atom on the saccharide), and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" or "carboxylate" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 4 to 10 carbon atoms and 1 to 4 heteroatoms selected from the group consisting of oxygen, nitrogen and sulfur within the ring. Such heteroaryl groups can have a single ring (e.g. pyridinyl or furyl) or multiple condensed rings (e.g. indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 2 to 10 ring carbon atoms and from 1 to 4 ring heteroatoms selected from the group consisting of nitrogen, sulfur, or oxygen. $C_x$ cycloalkyl or heterocycloalkyl refers to a group having x number of ring carbon atoms excluding the ring heteroatoms. Heterocycle encompasses single ring or multiple condensed rings, including fused, bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, dexahydroindole, dihydropyridine, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, imidazolinone, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Phthalimido" refers to the group

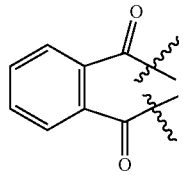

Phthalimide functional groups, sometimes used as a protecting group, are well known in the art and can be generated by covalently bonding a nitrogen atom to a C$_6$H$_4$(CO)$_2$ group.

"Spirocyclic ring system" refers to a ring system with two rings that has a single ring carbon atom in common to both rings. Herein used the term bicyclic can incorporate up to four heteroatoms in either ring.

"Bicyclic ring" or "Bicyclic ring system" refers to a ring system with two rings that has two ring carbon atoms in common, and which can located at any position along either ring. Herein used the term bicyclic ring system can incorporate up to four heteroatoms in either ring.

"Sulfinyl" refers to the divalent group —SO—.

"Sulfonyl" refers to the divalent group —S(O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluoromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluoromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substitution" or "substitution" or "substituted" generally refers groups which are covalently bonded to an atom to replace a hydrogen atom. The atom in this general context can be a carbon atom or a heteroatom, for example a nitrogen atom.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Tautomer" refers to alternate forms of a compound that differ in the position of a proton, such as enol-keto and imine-enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluromethyl, fluoromethyl and the like.

4.2. Additional Interpretational Conventions

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P and $^{35}$S are thus within the scope of the present technology. Procedures for inserting such labels into the compounds of the present technology will be readily apparent to those skilled in the art based on the disclosure herein.

Unless the specific stereochemistry is expressly indicated, all chiral, diastereomeric, and racemic forms of a compound are intended. Thus, compounds described herein include enriched or resolved optical isomers at any or all asymmetric atoms as are apparent from the depictions. Racemic mixtures, and d or l enriched stereomeric mixtures, as well as the individual optical isomers can be isolated or synthesized so as to be substantially free of their enantiomeric or diastereomeric partners, and these stereoisomers are all within the scope of the present technology.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

Herein any substituted functional group is substituted at from one to three different positions, and those one to three substituting groups are capable of each independently being substituted at one to three positions, wherein any and each substituting group is independently selected from the group consisting of: halogen, hydroxyl, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, acyl, acylamino, aminocarbonylamino, aminoacyl, acyloxy, amino, substituted amino, aminocarbonyl, aminothiocarbonyl, aminoacyl carbonyloxy, aminocarbonylamino, aminothiocarbonylamino, aminocarbonyloxy, aminosulfonyl, aminosulfonyloxy, aminosulfonylamino, amidino, $C_1$-$C_8$ alkoxy, substituted $C_1$-$C_8$ alkoxy, $C_3$-$C_7$ aryl, substituted $C_3$-$C_7$ aryl, $C_3$-$C_7$ aryloxy, substituted $C_3$-$C_7$ aryloxy, $C_3$-$C_7$ arylthio, substituted $C_3$-$C_7$ arylthio, carboxyl, carboxyl ester, (carboxyl ester)amino, (carboxyl ester)oxy, $C_3$-$C_{10}$ cycloalkyl, substituted $C_3$-$C_{10}$ cycloalkyl, $C_3$-$C_7$ heterocycloalkyl, guanidino, substituted guanidino, $C_3$-$C_7$ heteroaryloxy, $C_3$-$C_7$ substituted heteroaryloxy, $C_3$-$C_7$ heteroarylthio, $C_3$-$C_7$ substituted heteroarylthio, sulfonyl, substituted sulfonyl, sulfinyl, substituted sulfinyl, sulfonyloxy, substituted sulfonyloxy, thioacyl, alkylthio, substituted alkylthio, $C_3$-$C_7$ heteroaryl, and substituted $C_3$-$C_7$ heteroaryl.

Herein any and all heteroaryl and heterocycloalkyl substituents may contain up to four heteroatoms selected from the group consisting of: O, N, and S, but do not contain the heteroatom-heteroatom bonds: O—O, O—S, N—S, N—O and S—S bonds. It is understood that in all substituted groups defined above, polymers arrived at by defining substituents with further substituents to themselves (e.g. substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be substituted one more time (at from one to three positions).

It is understood that the definitions presented herein are not intended to include impermissible substitution patterns (e.g. methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein, is intended merely to better illuminate the embodiments and does not pose a limitation on the scope of the claims unless otherwise stated. No language in the specification should be construed as indicating any non-claimed element as essential.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

4.3. Processes 4.3.1. Total Syntheses

In a first aspect, the disclosure provides for a total synthesis of florylpicoxamid. In some aspects, the disclosure provides for a process of manufacturing florylpicoxamid wherein the process returns the amount of florylpicoxamid made is greater than or equivalent to five hundred (500) grams (g). In some aspects, the process of manufacturing florylpicoxamid returns greater than or equivalent to one (1) kilogram (kg) of florylpicoxamid. In some aspects, the disclosure provides for a process of manufacturing florylpicoxamid wherein the process returns five hundred (500) grams or one (1) kg of florylpicoxamid where the amount of each of the starting materials, i.e. compound II, compound III, pivalic anhydride, and NMI or DMAP is such that it corresponds with the amounts needed based on the reaction stoichiometry and % yield disclosed in the addition reaction disclosed in the Examples section herein, and assuming that any following steps, if needed, are nearly quantitative, i.e. any deprotection and/or amidation and/or reduction and/or acylation reactions needed to go from compound II all the way to florylpicoxamid are ≥~80%, ~85%, ~90%, or ~95% in yield; and therefore the amount of each of the starting material compounds may be calculated or adjusted according to the expected yield, as described above, from those reactions. In some aspects, the disclosure provides for a process of manufacturing enantiomeric and/or diastereomeric enriched synthetic intermediates useful for the total synthesis of florylpicoxamid.

In one aspect, the disclosure provides for a process of manufacturing florylpicoxamid wherein the process comprises:

1) mixing the following compounds:

a) a compound of formula II:

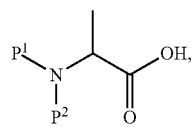

or a salt thereof, b)

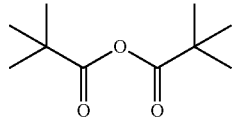

(pivalic anhydride), c)

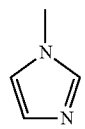

(N-methylimidazole) or

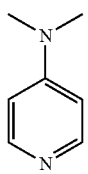

(DMAP); and d) a compound of formula III:

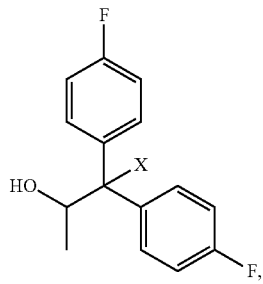

or a salt thereof;

wherein each of $P^1$ and $P^2$ is independently selected from the group consisting of: hydrogen and protecting group (Pg), provided that both $P^1$ and $P^2$ are not hydrogen;

X is selected from the group consisting of: hydrogen, halogen, hydroxy, acyloxy, carboxyl ester)oxy, thiol, alkylthio, sulfinylamino, sulfinyloxy and sulfonyloxy;

2) de-protecting the protecting group from either of $P^1$ and/or $P^2$; to form a compound of formula IV:

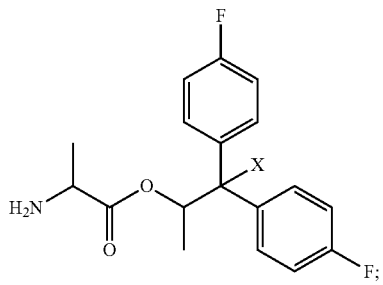

3) coupling

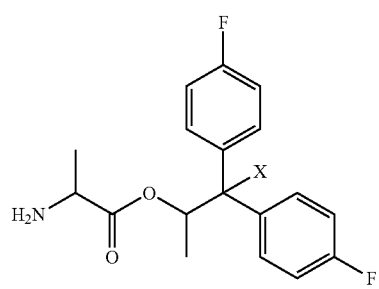

with either

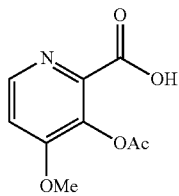 or 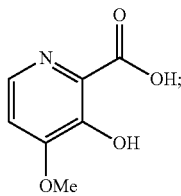

4) optionally acetylating the

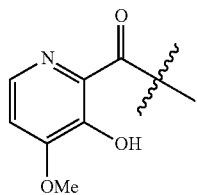 [SMILES: *C(=O)c1nccc(OC)c1O]

moeity; and
5) performing the following transformation at any time before or after any of steps 2-4:
optionally reducing the X group of the

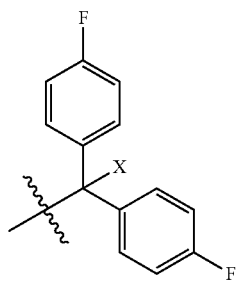

moiety so that X is hydrogen.

In one aspect, the disclosure provides for a process of manufacturing a compound according to:

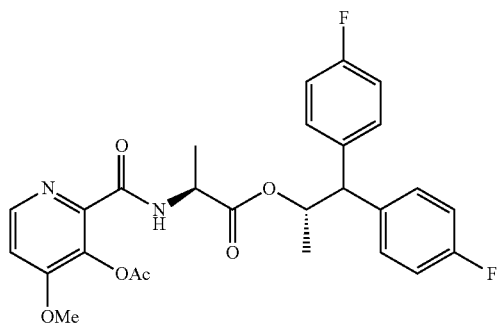 [SMILES: COc1ccnc(C(=O)N[C@@H](C)C(=O)O[C@@H](C)C(c2ccc(F)cc2)c2ccc(F)cc2)c1OC(C)=O]

(enatiomerically and/or diastereomerically enriched florylpicoxamid) wherein the process comprises:
1) mixing the following compounds:
a) a compound of formula II:

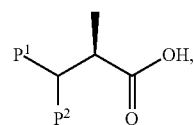

IIa or a salt thereof,
b)

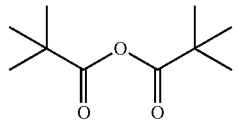

(pivalic anhydride),
c)

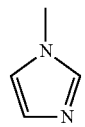

(N-methylimidazole) or

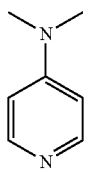

(DMAP); and
d) a compound of formula III:

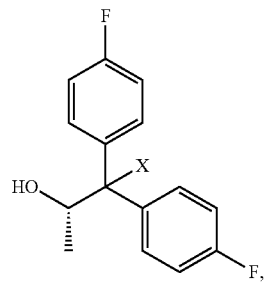

IIIa or a salt thereof;
wherein
each of $P^1$ and $P^2$ is independently selected from the group consisting of: hydrogen and protecting group (Pg), provided that both $P^1$ and $P^2$ are not hydrogen;

X is selected from the group consisting of: hydrogen, halogen, hydroxy, acyloxy, carboxyl ester)oxy, thiol, alkylthio, sulfinylamino, sulfinyloxy and sulfonyloxy;

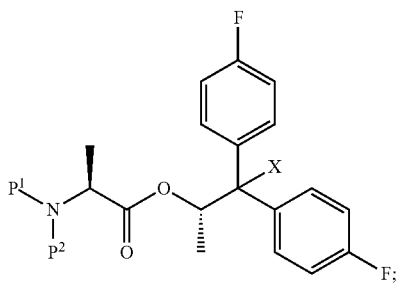

IVb to form a compound of formula IVb:

2) de-protecting the compound of formula IVb to form a compound of formula IV:

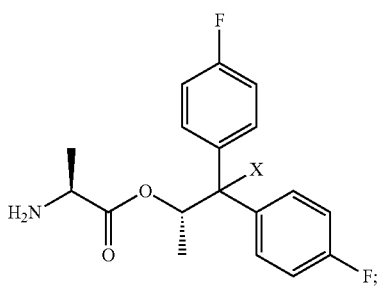

IVa 3) coupling

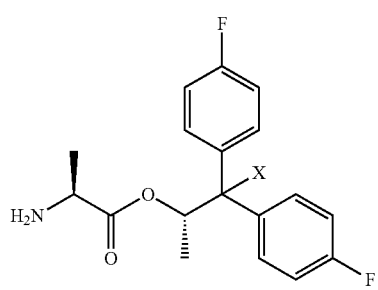

IVa with either

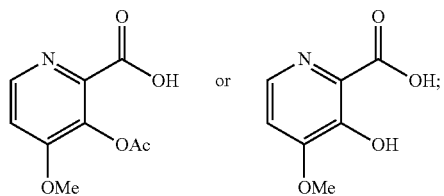 [SMILES: COc1ccnc(C(=O)O)c1OC(C)=O ; COc1ccnc(C(=O)O)c1O]

4) optionally acetylating the

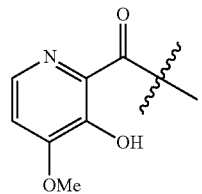 [SMILES: *C(=O)c1nccc(OC)c1O]

moeity; and 5) performing the following transformation at any time before or after any of steps 2-4:
   optionally reducing the X group of the

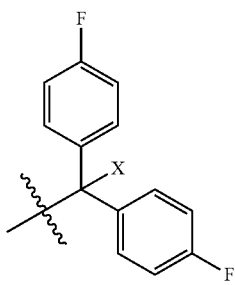

moiety so that X is hydrogen.

In one aspect, the disclosure provides for a process of manufacturing florylpicoxamid wherein the process comprises:

1) mixing the following compounds:
   a) a compound of formula II:

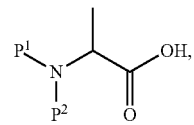

II or a salt thereof, b)

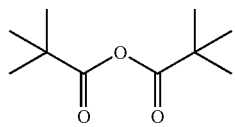

(pivalic anhydride), c)

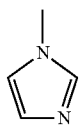

(N-methylimidazole) or

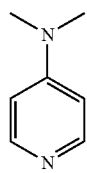

(DMAP); and d) a compound of formula III:

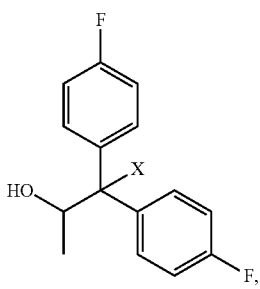

or a salt thereof;
wherein
each of P¹ and P² is independently selected from the group consisting of: hydrogen,

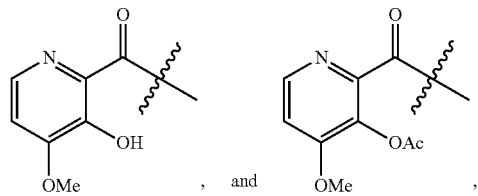 [SMILES: *C(=O)c1nccc(OC)c1O ; *C(=O)c1nccc(OC)c1OC(C)=O]

provided that both P¹ and P² are not hydrogen;

X is selected from the group consisting of: hydrogen, halogen, hydroxy, acyloxy, carboxyl ester)oxy, thiol, alkylthio, sulfinylamino, sulfinyloxy and sulfonyloxy; and 2) optionally acetylating the

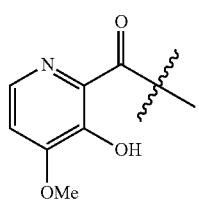 [SMILES: *C(=O)c1nccc(OC)c1O]

moeity and/or optionally reducing the X group of the

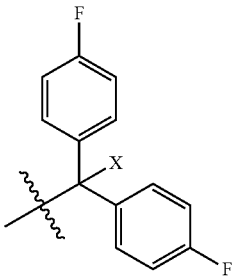

moiety so that X is hydrogen.

In one aspect, the disclosure provides for a process of manufacturing florylpicoxamid wherein the process comprises:

1) mixing the following compounds:

a)

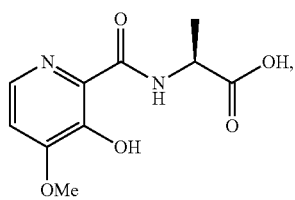 [SMILES: COc1ccnc(C(=O)N[C@@H](C)C(=O)O)c1O]

or a salt thereof, b)

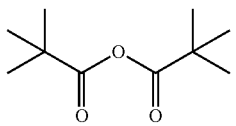

(pivalic anhydride), c)

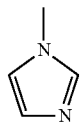

(N-methylimidazole) or

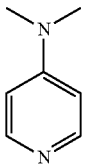

(DMAP); and
d) a compound of formula III:

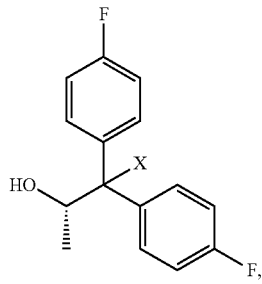

IIIa or a salt thereof;
wherein
X is selected from the group consisting of: hydrogen, halogen, hydroxy, acyloxy, carboxyl ester)oxy, thiol, alkylthio, sulfinylamino, sulfinyloxy and sulfonyloxy; and 2) acetlyating the

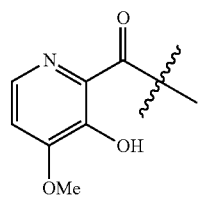 [SMILES: *C(=O)c1nccc(OC)c1O]

moeity; and 3) optionally reducing, before or after step 2, the X group of the

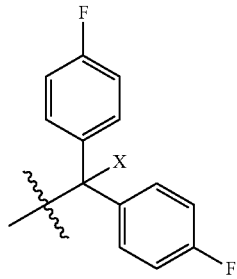

moiety so that X is hydrogen.

In one aspect, the disclosure provides for a process of manufacturing florylpicoxamid wherein the process comprises mixing the following compounds:

a)

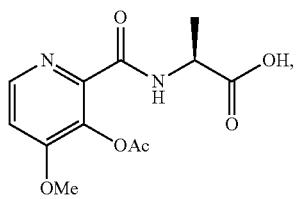 [SMILES: COc1ccnc(C(=O)N[C@@H](C)C(=O)O)c1OC(C)=O]

or a salt thereof, b)

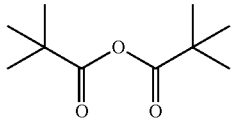

(pivalic anhydride), c)

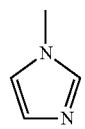

(N-methylimidazole) or

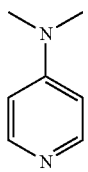

(DMAP); and
d) a compound of formula III:

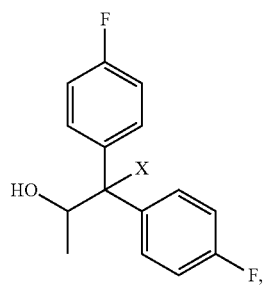

III or a salt thereof;
wherein
X is selected from the group consisting of: hydrogen, halogen, hydroxy, acyloxy, carboxyl ester)oxy, thiol, alkylthio, sulfinylamino, sulfinyloxy and sulfonyloxy.

In one aspect, the disclosure provides for a process of manufacturing a compound according to formula I wherein the process comprises mixing the following compounds:

27
a)
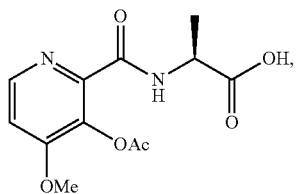 [SMILES: COc1ccnc(C(=O)N[C@@H](C)C(=O)O)c1OC(C)=O]
or a salt thereof,
b)
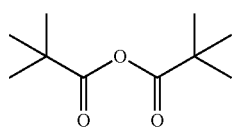
(pivalic anhydride),
c)
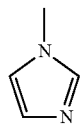
(N-methylimidazole) or
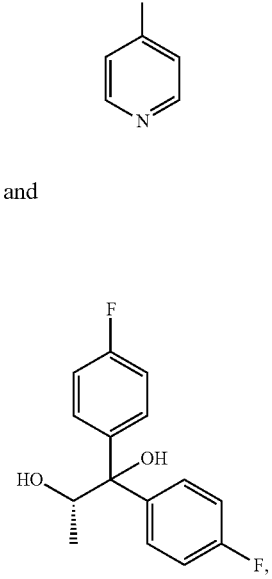
(DMAP); and
d)
or a salt thereof.
In one aspect, the disclosure provides for a process of manufacturing a compound according to formula I, wherein the process comprises mixing the following compounds:
28
a)
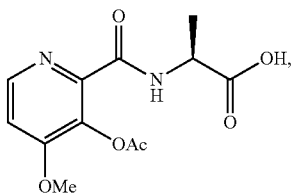 [SMILES: COc1ccnc(C(=O)N[C@@H](C)C(=O)O)c1OC(C)=O]
or a salt thereof,
b)
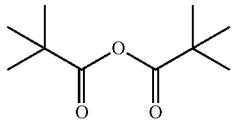
(pivalic anhydride),
c)
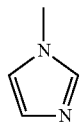
(N-methylimidazole) or
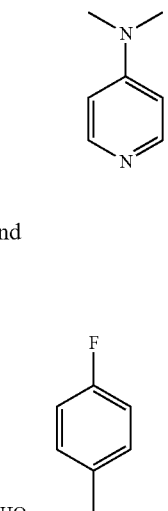
(DMAP); and
d)
or a salt thereof.

In some aspects, the disclosure provides for methods of manufacture of a compound according to formula I:

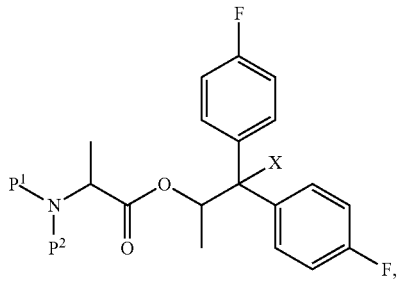

the process comprising: mixing the following compounds:
a) a compound of formula II:

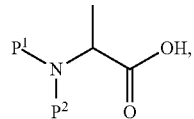

or a salt thereof,
b)

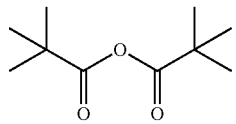

(pivalic anhydride),
c) an amine-containing acylation catalyst; and
d) a compound of formula III:

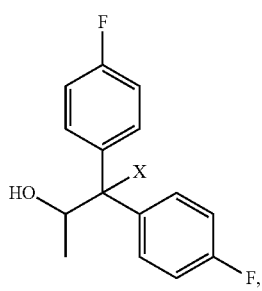

or a salt thereof;
wherein
each of $P^1$ and $P^2$ is independently selected from the group consisting of: hydrogen,

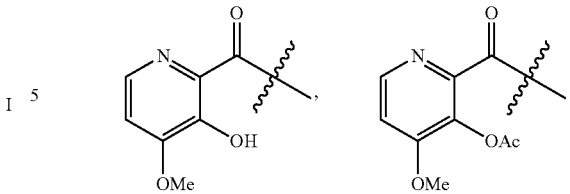

and protecting group (Pg), provided that both $P^1$ and $P^2$ are not hydrogen;
X is selected from the group consisting of: hydrogen, halogen, hydroxy, acyloxy, carboxyl ester)oxy, thiol, alkylthio, sulfinylamino, sulfinyloxy and sulfonyloxy.

In various aspects, the disclosure provides for a method of manufacture of a compound according to any one of the embodiments disclosed herein. In various aspects, the disclosure provides for a method of manufacture of a compound wherein the process for the manufacture is any one of the process embodiments described herein.

4.3.2. Addition Reaction

In broad strokes, herein disclosed are processes for coupling and esterifying a protected amino acid compound, i.e. an addition reaction including a synthon with a chiral alcohol. A little more specifically, the addition reaction or esterification reaction of an N-protected alanine with a 1,1-bis(aryl)-substituted 1,2-diol is disclosed. The protected amino acid derivative and the alcohol are both chiral, and as such basic conditions needed for esterification, of these two for example, and most very often leads to epimerization of one of or both of chiral centers. The inventors have found processes to overcome this difficulty. Racemization can plague this process upwards 10% racemization. Further, this process can utilize the improved safety of N-methyl imidazole, since it is less toxic than other acyl catalysts, and it is a liquid at room temperature, meaning that it is safer and easier to use in manufacturing setting because it can be piped in, and of course, that does not mean other acyl catalysts cannot be used, but rather that the afore mentioned aspect is a nice little feature of the current processes described herein.

In some aspects, the disclosure provides a process comprising esterification of an alanine protected synthon with a chiral alcohol. In some of those aspects, the process is on an industrial scale; e.g. on a 1 or 2 kilogram scale of starting material of the reaction.

In some aspects, the disclosure provides a process wherein the amine-containing acylation catalyst is (1,4-diazabicyclo[2.2.2]octane) (DABCO). In some aspects, the disclosure provides a process wherein the amine-containing acylation catalyst is N-methylimidazole (NMI). In some aspects, the disclosure provides a process wherein the amine-containing acylation catalyst is imidazole. In some aspects, the disclosure provides a process wherein the amine-containing acylation catalyst is 4-pyrrolidinopyridine (PPY). In some aspects, the disclosure provides a process wherein the amine-containing acylation catalyst is Quinidine, or an analog thereof.

In some aspects, the disclosure provides a process wherein the amine-containing acylation catalyst is selected from the group consisting of: DMAP, PPY, Quinidine and NMI.

In some aspects, a process is provided wherein X is a leaving group. In some aspects, a process is provided wherein X is OTs or OMs. In some aspects, a process is provided wherein X is a halogen. In some aspects, a process is provided wherein X is Cl. In some aspects, a process is provided wherein X is OSO₃H, or a salt thereof. In some aspects, a process is provided wherein X is a sulfonate ester that is covalently bonded such that: —OSO₃R. In some aspects, a process is provided wherein X is OH. In some aspects, a process is provided wherein X is a silyl ether that is covalently bonded such that: —OSiR₃. In some aspects, a process is provided wherein X is OTMS. In some aspects, a process is provided wherein X is OTBS. In some aspects, a process is provided wherein X is OTBDPS.

In some aspects, a process is provided wherein Pg is silyl.

In some aspects, a process is provided wherein N-Pg forms a sulfonamide group. In some aspects, N-Pg forms a carbamate group. In some aspects, N-Pg forms an amide group. In some aspects, N-Pg forms a urea group.

In some aspects, a process is provided wherein Pg is selected from the group consisting of: Boc, Fmoc, acetamide, trifluoroacetamide, tosylate, mesylate, and allyl.

In one aspect, the disclosure provides for a process of manufacturing

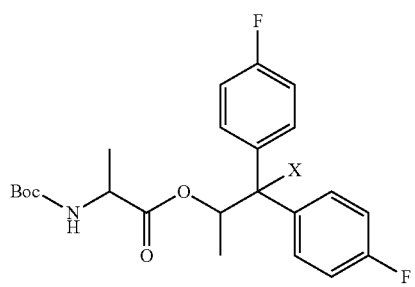

wherein the process comprises mixing the following compounds:

a)

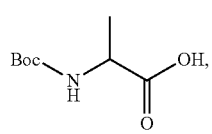

or a salt thereof, b)

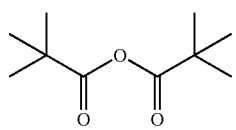

(pivalic anhydride), c)

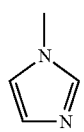

(N-methylimidazole) or

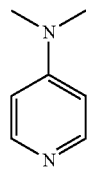

(DMAP); and d) a compound:

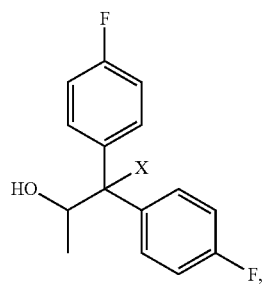

or a salt thereof;

wherein X is selected from the group consisting of: hydrogen, halogen, hydroxy, acyloxy, carboxyl ester)oxy, thiol, alkylthio, sulfinylamino, sulfinyloxy and sulfonyloxy.

In one aspect, the disclosure provides for a process of manufacturing

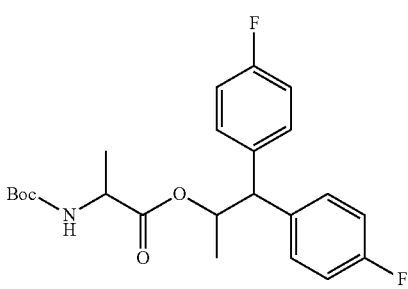 [SMILES: CC(NC(=O)OC(C)(C)C)C(=O)OC(C)C(c1ccc(F)cc1)c1ccc(F)cc1]

wherein the process comprises mixing the following compounds:

a)

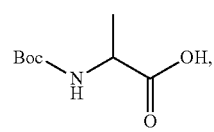

or a salt thereof,
b)

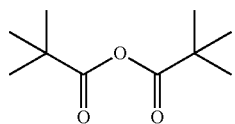

(pivalic anhydride),
c)

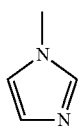

(N-methylimidazole) or

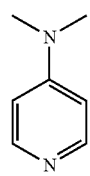

(DMAP); and

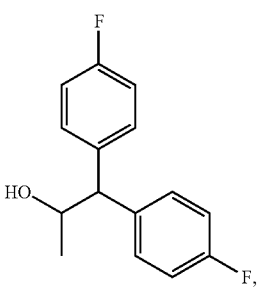

or a salt thereof.

In one aspect, the disclosure provides for a process of manufacturing

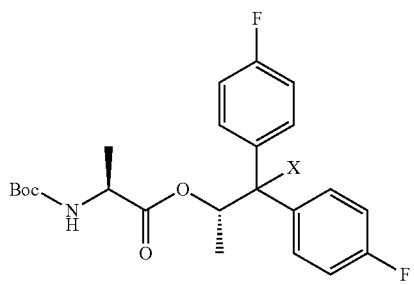

wherein the process comprises mixing the following compounds:
a)

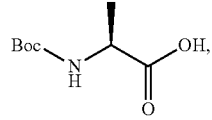

or a salt thereof,
b)

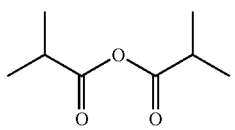

(pivalic anhydride),
c)

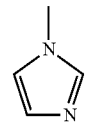

(N-methylimidazole) or

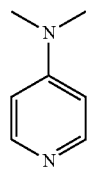

(DMAP); and
d) a compound:

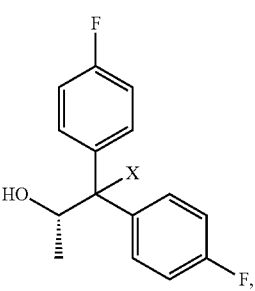

or a salt thereof;
wherein X is selected from the group consisting of: hydrogen, halogen, hydroxy, acyloxy, carboxyl ester)oxy, thiol, alkylthio, sulfinylamino, sulfinyloxy and sulfonyloxy.

In one aspect, the disclosure provides for a process of manufacturing

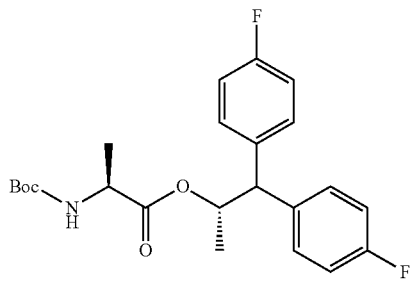 [SMILES: C[C@H](NC(=O)OC(C)(C)C)C(=O)O[C@@H](C)C(c1ccc(F)cc1)c1ccc(F)cc1]

wherein the process comprises mixing the following compounds:

a)

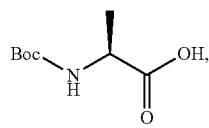

or a salt thereof, b)

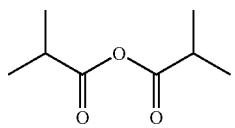

(pivalic anhydride), c)

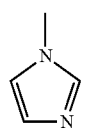

(N-methylimidazole) or

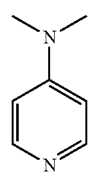

(DMAP); and d)

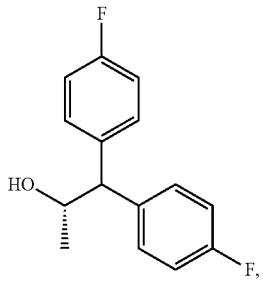 [SMILES: C[C@H](O)C(c1ccc(F)cc1)c1ccc(F)cc1]

or a salt thereof.

In one aspect, the disclosure provides for a process of manufacturing

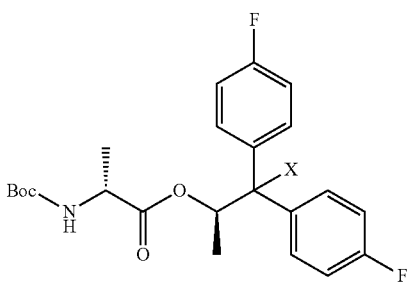

wherein the process comprises mixing the following compounds:

a)

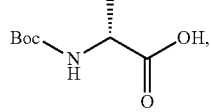

or a salt thereof, b)

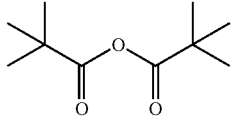

(pivalic anhydride), c)

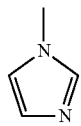

(N-methylimidazole) or

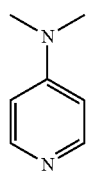

(DMAP); and d) a compound:

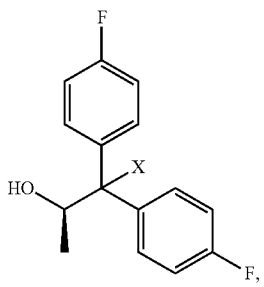

or a salt thereof;

wherein X is selected from the group consisting of: hydrogen, halogen, hydroxy, acyloxy, carboxyl ester)oxy, thiol, alkylthio, sulfinylamino, sulfinyloxy and sulfonyloxy.

In one aspect, the disclosure provides for a process of manufacturing

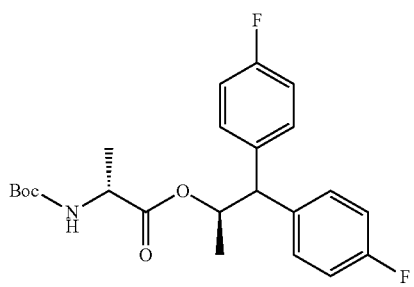 [SMILES: C[C@@H](NC(=O)OC(C)(C)C)C(=O)O[C@H](C)C(c1ccc(F)cc1)c1ccc(F)cc1]

wherein the process comprises mixing the following compounds:

a)

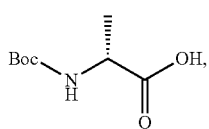

or a salt thereof, b)

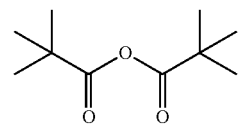

(pivalic anhydride), c)

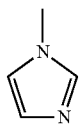

(N-methylimidazole) or

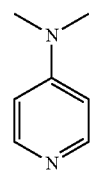

(DMAP); and or a salt thereof.

4.3.3. Reaction Conditions

In some aspects, the disclosure provides a process for preparing the compounds disclosed herein, the process comprising mixing synthons together, neat or in an organic solvent, and extracting out the product by partitioning the organic solvent with water.

In some aspects, the disclosure provides a process wherein the organic solvent is protic. In some aspects, the disclosure provides a process wherein the organic solvent is aprotic. In some aspects, the disclosure provides a process wherein the organic solvent is heptanes, dichloromethane, hexanes, cyclohexane, toluene, acetonitrile, tetrahydrofuran, 2-methylhydrofuran, ethyl acetate, dichloromethane (DCM), dichloroethane (DCE), or methylcyclohexane. In some aspects, the disclosure provides a process wherein the mixture contains an aprotic organic solvent selected from the group consisting of: hepantes, THF (tetrahydrofuran) and diethyl ether.

In some aspects, the disclosure provides a process wherein the process includes one or more organic co-solvents. In some aspects, the disclosure provides a process wherein the mixture contains dimethylformamide (DMF) as a solvent. In some aspects, the disclosure provides a process wherein the mixture contains dimethylformamide (DMF) as a solvent and a co-solvent. In some aspects, the disclosure provides a process wherein the mixture contains heptanes as a solvent and a co-solvent. In some aspects, the disclosure provides a process wherein the mixture contains heptanes as a solvent and THF co-solvent. In some aspects, the disclosure provides a process wherein the mixture contains heptanes as a solvent and DCM co-solvent.

In some aspects, the disclosure provides a process wherein the amount of amine-containing acylation catalyst is 20 mol %, 18 mol %, 16 mol %, 14 mol %, 12 mol %, 10 mol %, 9 mol %, 8 mol %, 7 mol %, 6 mol %, 5 mol %, 4 mol %, 3 mol %, 2 mol %, or 1 mol % based on the amount of compound III. In some aspects, the amount of acylation catalyst is 0.9 mol %, 0.8 mol %, 0.7 mol %, 0.6 mol %, 0.5 mol %, 0.4 mol %, 0.3 mol %, 0.2 mol %, or 0.1 mol % based on the amount of compound III. In some aspects, the disclosure provides a process wherein the amount of acylation catalyst is 0.05 or 0.01 mol % based on the amount of compound III.

In some aspects, a process is provided to make the compound of formula I wherein the process further comprises heating of the mixture. In some aspects, the heating is performed to at least 25° C., 26° C., 27° C., 28° C., 29° C., 30° C., 40° C., 50° C., 60° C., 70° C., 80° C., 90° C., 100° C., 110° C., or 120° C.

In some aspects, the disclosure provides a process wherein the amount of pivalic anhydride is from 0.5-1.5 equivalents based on compound formula III.

In some aspects, the disclosure provides a process wherein the amount of compound II is from 0.5-1.5 equivalents based on compound formula III.

In one aspect, the disclosure provides a process wherein the amount of each of the compounds mixed is according to: 1.2 equivalents (by mol) pivalic anhydride, 1.1 equivalents (by mol) Boc-alanine, 1 equivalent (by mol) compound III and 5 mol % NMI or DMAP. In one aspect, the disclosure provides a process wherein the amount of each of the compounds mixed is according to: 1.2 equivalents (by mol) pivalic anhydride, 1.1 equivalents (by mol) Boc-alanine, 1 equivalent (by mol) compound III and 1 mol % NMI or DMAP.

In one aspect, the disclosure provides a process wherein the amount of each of the compounds mixed is according to: 1.5 equivalents (by mol) pivalic anhydride, 1.5 equivalents (by mol) Boc-alanine, 1 equivalent (by mol) compound III and 0.5 mol % NMI or DMAP.

4.3.4. Exemplary Procedure for the Process

In one aspect, the process can be affected by a general methodology, the method comprising adding the components into a reactor or mixing tank: chiral alcohol diol, protected amino acid derivative, solvent, organic amine catalyst (1-methylimidazole or DMAP, preferably) and pivalic anhydride under inert atmosphere. Conditions for this reaction may not be strictly anhydrous, i.e. a small amount of water, say less than 1%, say less than 0.5%, say less than 0.25%, or say less than 0.1%, will not significantly hinder the reaction.

Next, this suspension is heated and monitored. The reaction mixture is allowed to cool to room temperature and an extraction solvent is added.

Ice-water is then dropped slowly into the mixture and after standing, the organic layer is separated and taken. The aqueous layer is extracted two more times and the combined organics are washed with a basic carbonate solution and brine. Finally, the combined organic layers are dried with magnesium sulfate.

4.4. Compounds

In a first aspect, the disclosure provides useful intermediates of or protected forms of the Florylpicoxamid.

4.4.1. Forms of Florylpicoxamid

In some aspects, the disclosure provides one particular enriched diastereomer of florylpicoxamid, or an intermediate thereof. In those aspects, the disclosure provides for a compound/mixture containing the diastereomerically enriched compound:

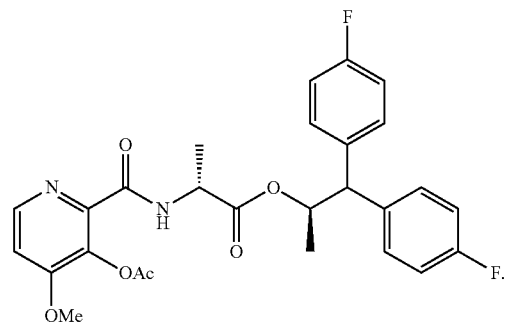 [SMILES: COc1ccnc(C(=O)N[C@H](C)C(=O)O[C@H](C)C(c2ccc(F)cc2)c2ccc(F)cc2)c1OC(C)=O]

In another aspect, the compound is:

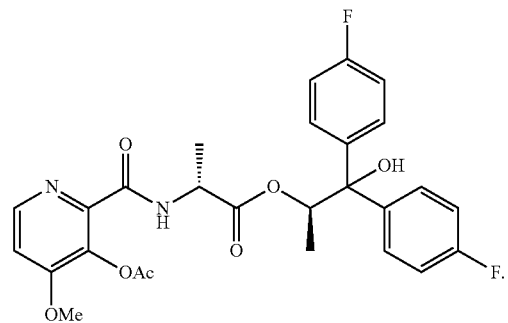 [SMILES: COc1ccnc(C(=O)N[C@H](C)C(=O)O[C@H](C)C(O)(c2ccc(F)cc2)c2ccc(F)cc2)c1OC(C)=O]

In another aspects, the compound is:

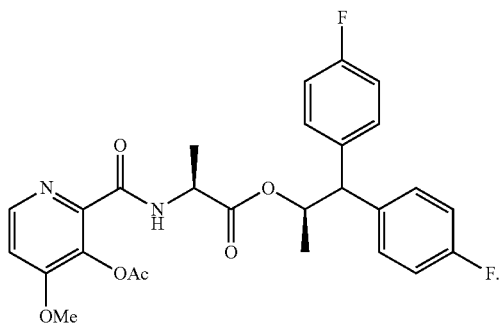 [SMILES: COc1ccnc(C(=O)N[C@@H](C)C(=O)O[C@H](C)C(c2ccc(F)cc2)c2ccc(F)cc2)c1OC(C)=O]

In another aspect, the compound is:

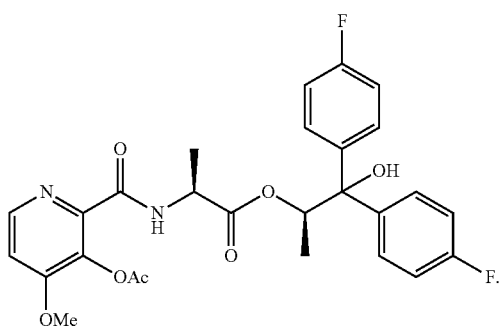 [SMILES: COc1ccnc(C(=O)N[C@@H](C)C(=O)O[C@H](C)C(O)(c2ccc(F)cc2)c2ccc(F)cc2)c1OC(C)=O]

In another aspect, the compound is:

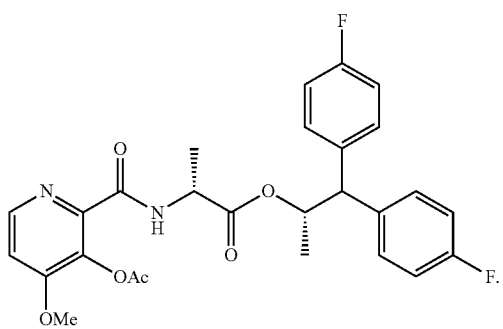 [SMILES: COc1ccnc(C(=O)N[C@H](C)C(=O)O[C@@H](C)C(c2ccc(F)cc2)c2ccc(F)cc2)c1OC(C)=O]

In another aspect, the compound is:

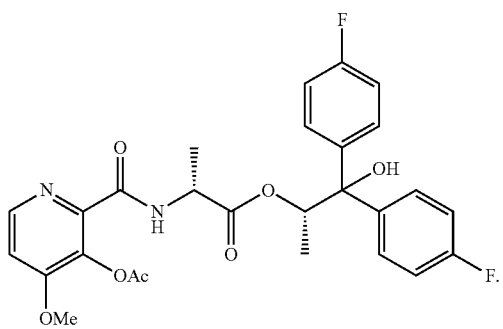 [SMILES: COc1ccnc(C(=O)N[C@H](C)C(=O)O[C@@H](C)C(O)(c2ccc(F)cc2)c2ccc(F)cc2)c1OC(C)=O]

In one aspect, the disclosure provides for protected forms of florylpicoxamid. Because the synthesis in the '764 patent has demonstrated that florylpicoxamid may be put together by a sequence of addition/elimination reactions following the peptide coupling (for example, the acylation of the hydroxyl moiety on the pyridine following the coupling or even the reduction of the tertiary alcohol of the 1,1-bis aryl moiety even after coupling the amino acid), herein the processes described work and support a total synthesis of florylpicoxamid. Certain functional groups may or may not be protected. These masked functionalities do not affect the total synthesis as is apparent from '764. Accordingly, the disclosure provides for such forms of the desired florylpicoxamid compound.

In some aspects, the protected form of florylpicoxamid has a Pg group on either the oxygen atom on the tertiary carbon connected to the bis-phenyl group or the nitrogen atom of the amide group or the oxygen atoms of the pyridine group. Such protected forms, for example, would be structurally within the formula of the following compound:

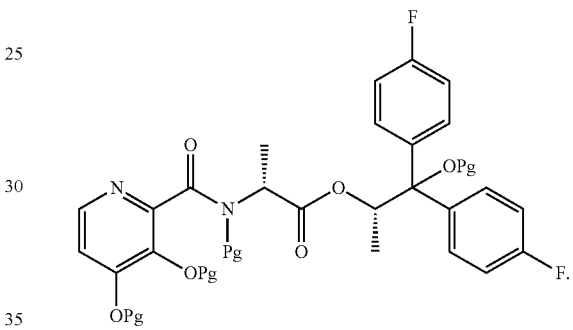

In one of those aspects, the protected florylpicoxamid has one or more Pg groups that is selected from the group consisting of: acyl, formyl, acylamino, aminocarbonyl, aminothiocarbonyl, aminosulfonyl, amidino, carboxy ester, benzyl, benzylidene, hydroxy, substituted sulfonyl, substituted sulfinyl, and sulfonyloxy. In some aspects, the protected florylpicoxamid has one or more Pg groups that is selected from the group consisting of: Boc, Ms, Ts, benzyl (—CH₂Ph), allyl

and vinyl.

In one aspect, the protected florylpicoxamid has one Pg group that is Boc. In one aspect the protected florylpicoxamid has one Pg group that is allyl

In some aspects, the protected florylpicoxamid has one Pg group that is Ts. In some aspects, the protected florylpicoxamid has two Pg groups and one that is Boc. In some aspects, the protected florylpicoxamid has one Pg group that is Fmoc. In some aspects, the protected florylpicoxamid has one Pg group that is trimethysilyl (TMS). In some aspects, the protected florylpicoxamid has one Pg group that is a vinyl functional group.

4.4.2. Synthetic Intermediates

In some aspects, the disclosure provides for a compound that is an intermediate to florylpicoxamid. In such an aspect, the compound is:

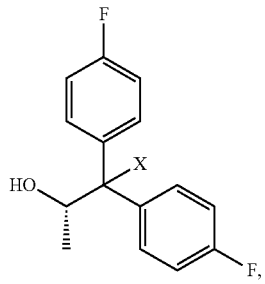

IIIa where X is a leaving group. In other aspects of formula IIIa, X is selected from the group consisting of: hydrogen, halogen, hydroxy, acyloxy, carboxyl ester)oxy, thiol, alkylthio, sulfinylamino, sulfinyloxy and sulfonyloxy. In another such aspect, the compound is:

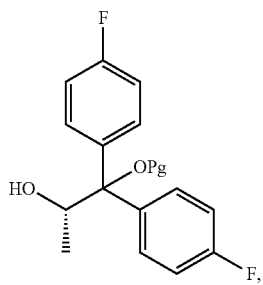

IIIb where Pg is a protecting group as described herein. In another such aspect, the compound is:

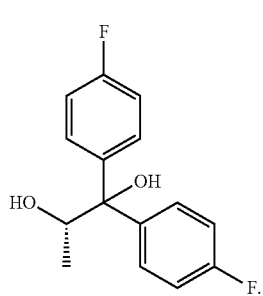

IIIc

In such an aspect, the compound is:

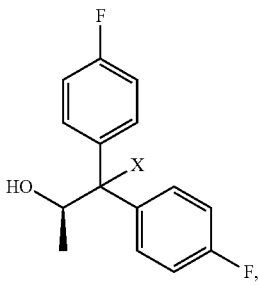

IIId where X is a leaving group. In other aspects of formula IIId, X is selected from the group consisting of: hydrogen, halogen, hydroxy, acyloxy, carboxyl ester)oxy, thiol, alkylthio, sulfinylamino, sulfinyloxy and sulfonyloxy. In another such aspect, the compound is:

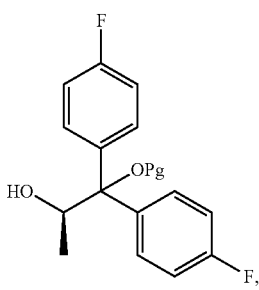

IIIe where Pg is a protecting group as described herein. In another such aspect, the compound is:

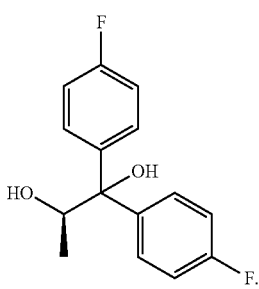

IIIf

In another such aspect, the compound is:

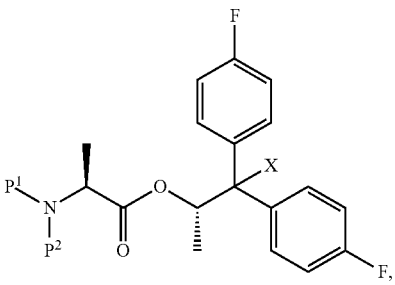

IVb where X is a leaving group. In another such aspect, the compound is:

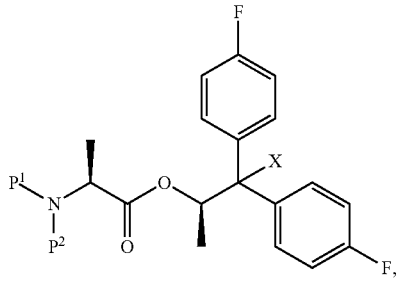
IVb2 where X is a leaving group. In another such aspect, the compound is:

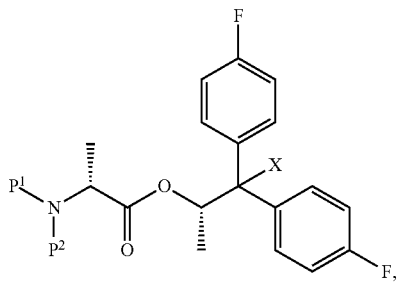
IVb3 where X is a leaving group. In another such aspect, the compound is:

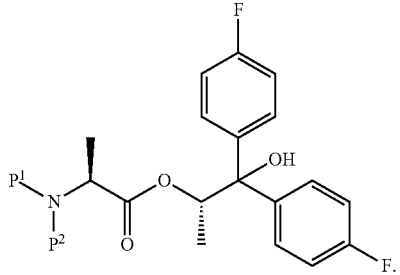
IVb4

In another such aspect, the compound is:

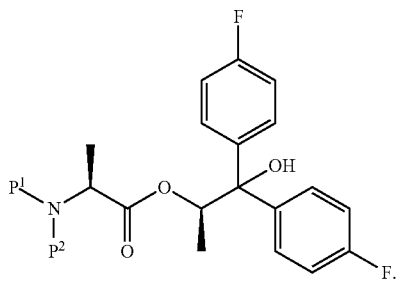
IVb5

In another such aspect, the compound is:

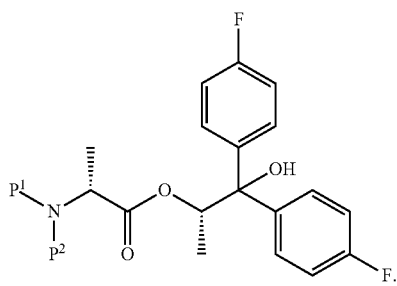
IVb6

In another such aspect, the compound is:

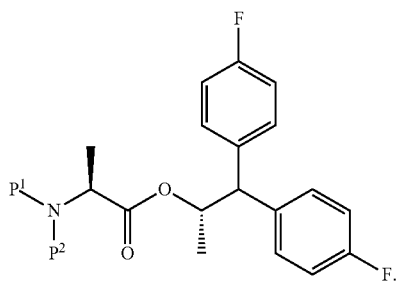
IVb7

In another such aspect, the compound is:

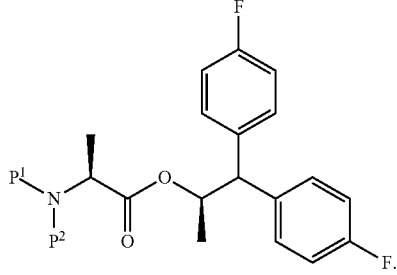
IVb8

In another such aspect, the compound is:

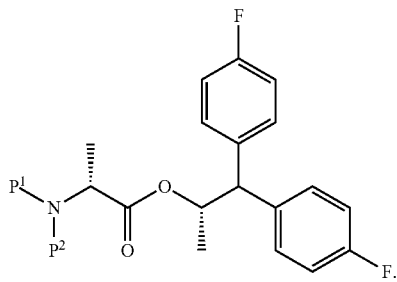
IVb9

In further aspects of formula IVb-9, X is selected from the group consisting of: hydrogen, halogen, hydroxy, acyloxy, carboxyl ester)oxy, thiol, alkylthio, sulfinylamino, sulfinyloxy and sulfonyloxy; and $P^1$ and $P^2$ are each independently selected from hydrogen and protecting group, provided that not both of $P^1$ and $P^2$ are hydrogen.

In another such aspect, the compound is:

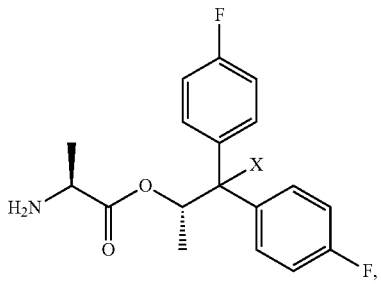

IVa where X is a leaving group. In another such aspect, the compound is:

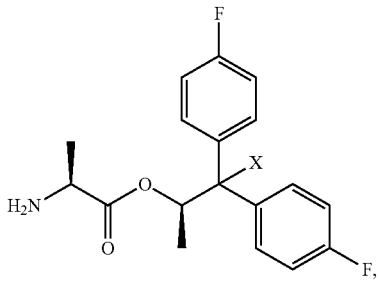

IVa2 where X is a leaving group. In another such aspect, the compound is:

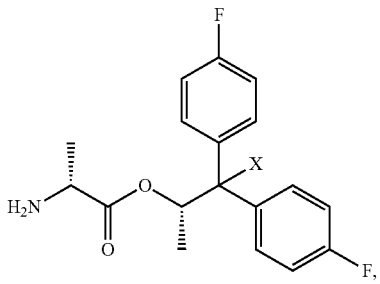

IVa3 where X is a leaving group. In further aspects of formula IVa-3, X is selected from the group consisting of: hydrogen, halogen, hydroxy, acyloxy, carboxyl ester)oxy, thiol, alkylthio, sulfinylamino, sulfinyloxy and sulfonyloxy.

In another such aspect, the compound is:

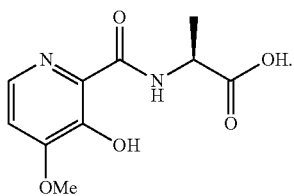

In another such aspect, the compound is:

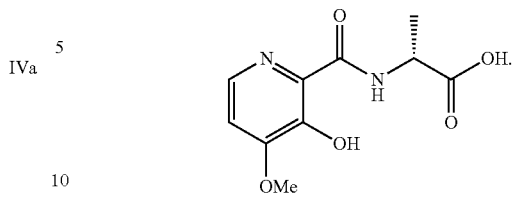

4.4.3. General Methods to Make and Use Enriched Florylpicoxamid and Synthetic Intermediates Compounds described herein can be prepared from readily available starting materials using the following general methods and procedures to the skilled artisan, e.g. those synthetic transformations described in the references already cited in this application.

Briefly, an amino acid, or derivative thereof (a compound of formula II or another such derivative compound possessing, a differing side chain functional group rather than methyl for the alanine derivative that is compound II), having of course as amino acids do, a chiral center, is "protected" by a reaction that put a functional group on the nitrogen atom of the N-terminus of the compound (of course the compound may or may not have another nitrogen atom at another position on the molecule). Such a protecting reaction is well known in the art and usually consists of placing the nucleophilic amine compound in an aprotic solvent with an organic base, such as trimethylamine, and an electrophilic compound as the protecting group partner, typically this is an acid chloride or carbonate or other electrophile compound, perhaps with a leaving group like a mesylate or chloride.

That protected product undergoes the addition reaction with pivalic anhydride, chiral alcohol and the amine-containing acylation catalyst as described in any one of the embodiments disclosed herein. The product is enantiomerically enriched and epimerization of either of the chiral centers is almost nil. That product, if needed at all, may be purified by chromatography or may be used directly in the next reaction: "deprotection".

Deprotection are also very, very well known in the art and typically consist of placing the protected compound in a solvent, protic or aprotic, under sufficient acidic or basic conditions so that only the protecting organic function group reacts and cleaves. Such conditions can be affected, for instance in the case of carbamate protection, by adding HCl in a solvent like dioxane.

Once the protecting functional group is unmasked, the resulting amine may be coupled to an appropriate pyridinyl carboxylic acid partner with an amidation reaction (conditions). These reactions are relatively straight forward and involve a placeholder group to form, like those resulting from adding a carbodiimide or an anhydride, and an amine-containing acylation catalyst for the reaction. Of course the pyridinyl carboxylic acid and/or the amine compounds may have a protecting group carried forward that will not react under these conditions and as such, may need to be removed by another deprotection reaction. Otherwise, such groups may be deprotected during the amidation reaction if the chemist wants to add in reagents that would increase or decrease the acidity or basicity sufficient to hydrolyze the group; or perhaps if the chemist adds in an additional, but specific reagent that will not harm the amidation reaction but will deprotect, for example upon release of the fluoride anion by adding in TBAF and deprotecting a silyl ether group on the amine compound or on the pyridinyl carboxylic acid compound. Such strategies can take care of two transformations "in situ" and are within the scope of this disclosure any step in any embodiment described herein. This is the case because synthetic organic chemistry and chemists have devised methods, described in the references already incorporated herein, that are benign enough to affect selective transformation of trivial functional groups, such as those for protection.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA), CombiChem (San Diego, Calif.). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

It will also be appreciated that where typical process conditions (i.e. reaction temperatures, times, mole ratios of reactants, solvents, pressures, etc.) are given to make these compounds, minor modifications to these process conditions can also be used unless otherwise stated. Optimum reaction conditions may vary with the particular reactant or solvent used, but such conditions can be determined by one skilled in the art by routine optimization procedures as long as the reagents stay the same.

Additionally, as will be apparent to those skilled in the art, conventional protecting groups may be necessary to prevent certain functional groups from undergoing undesired reactions. Herein it is understood that amino, keto, thio, hydroxyl, and any other necessary protecting groups and their methods of deprotection are known in the art, such as those described in T. W. Greene and P. G. M. Wutz, *Protecting Groups in Organic Synthesis*, Third Edition, Wiley, New York, 1999, which is incorporated in its entirety along with the references cited therein.

If the compounds described herein contain one or more chiral centers, such compounds can be prepared or isolated as pure stereoisomers, i.e. as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

4.5. Mixtures

In another aspects, mixtures are provided that comprise at least two or more compounds as described herein. That is mixtures are provided that are enriched in one desired compound, as described herein, with the impurity being the undesired enantiomers and/or diastereomers of that compound, or another chiral compound, which may be an intermediate in the desired compounds that was carried forward in the synthesis of the desired compound, or is another chiral compound that is unrelated to the synthesis or starting material. Thus, mixtures are provided that are enantiomerically and/or diastereomerically enriched in any one of the compounds as described herein.

In some aspects, mixtures are provided in which

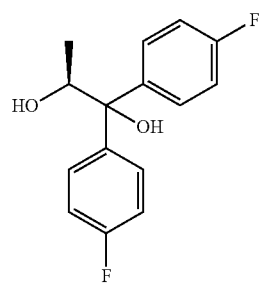 [SMILES: C[C@H](O)C(O)(c1ccc(F)cc1)c1ccc(F)cc1]

is the only impurity, or is one of two impurities, or is one or three or more impurities.

In some aspects, mixtures are provided in which

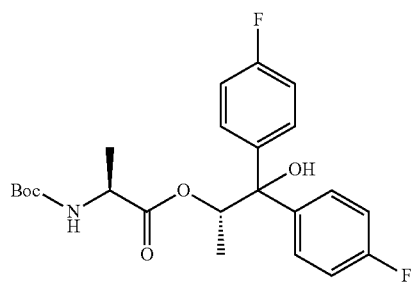 [SMILES: C[C@H](NC(=O)OC(C)(C)C)C(=O)O[C@@H](C)C(O)(c1ccc(F)cc1)c1ccc(F)cc1]

is the only impurity, or is one of two impurities, or is one or three or more impurities.

In some aspects, mixtures are provided in which

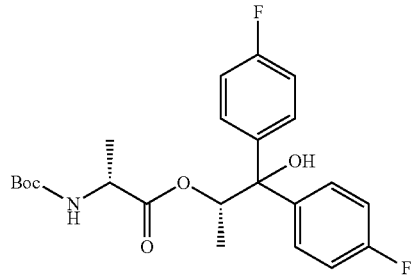 [SMILES: C[C@H](OC(=O)[C@@H](C)NC(=O)OC(C)(C)C)C(O)(c1ccc(F)cc1)c1ccc(F)cc1]

is the only impurity, or is one of two impurities, or is one or three or more impurities.

In some aspects, mixtures are provided in which

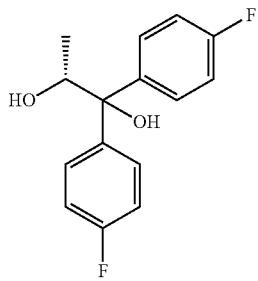 [SMILES: C[C@@H](O)C(O)(c1ccc(F)cc1)c1ccc(F)cc1]

is the only impurity, or is one of two impurities, or is one or three or more impurities.

In some aspects, mixtures are provided in which

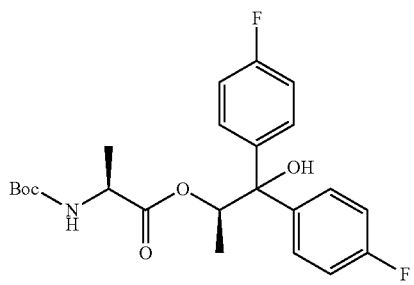 [SMILES: C[C@H](NC(=O)OC(C)(C)C)C(=O)O[C@H](C)C(O)(c1ccc(F)cc1)c1ccc(F)cc1]

is the only impurity, or is one of two impurities, or is one or three or more impurities.

In some aspects, mixtures are provided that comprise at least two or more compounds as described herein and are enantiomerically and/or diastereomerically enriched in one compound, as described herein, with an impurity from 0.01% to: no more than 0.1 mol %, no more than 0.5 mol %, no more than 1 mol %, no more than 2 mol %, no more than 3 mol %, or no more than 4 mol %. In some aspects, mixtures are enriched by about 95%, 96%, 97%, 98%, 99%, 99.5%, 99.7% or 99.9% enantiomeric excess (ee). In some aspects, mixtures are enriched by about 95%, 96%, 97%, 98%, 99%, 99.5%, 99.7% or 99.9% diastereomeric excess (de).

In some aspects, mixtures are provided that comprise at least two or more compounds as described herein and are enantiomerically and/or diastereomerically enriched with a compound of formula I with an impurity from 0.01% to: no more than 0.1 mol %, no more than 0.5 mol %, no more than 1 mol %, no more than 2 mol %, no more than 3 mol %, or no more than 4 mol %. In some aspects, mixtures are enriched by about 95%, 96%, 97%, 98%, 99%, 99.5%, 99.7% or 99.9% enantiomeric excess (ee). In some aspects, mixtures are enriched by about 95%, 96%, 97%, 98%, 99%, 99.5%, 99.7% or 99.9% diastereomeric excess (de).

In various embodiments, the mixture comprises one or more compounds as described herein. In other embodiments, the mixture comprises a plurality of compounds as described herein. In certain of these latter embodiments, the mixture comprises 2, 3, 4, or 5 or more of the herein described compounds.

In certain aspects, the mixture comprises one or more compounds as described herein, and Florylpicoxamid or salt thereof. In various embodiments, the mixture comprises 1, 2, 3, 4, or 5 compounds as described herein, and Florylpicox-amid or a salt thereof. In various embodiments, the mixture comprises 1, 2, 3, 4, or 5 compounds as described herein, and a protected form of Florylpicoxamid or a salt thereof.

The skilled artisan will appreciate that these percentages for purity are based and calculated from the desired compound. Such determinations are routine in the field and examples can be found in syntheses and descriptions in the texts and references that have been cited herein.

5. EXAMPLES

The following synthetic and biological examples are offered to illustrate this the present technology and are not to be construed in any way as limiting the scope of this the present technology. Unless otherwise stated, all temperatures are in degrees Celsius.

The examples are offered for illustrative purposes only, and are not intended to limit the scope of the present invention in any way. Efforts have been made to ensure accuracy with respect to numbers used (e.g. amounts, temperatures, etc.), but some experimental error and deviation should, of course, be allowed for.

The practice of the present invention will employ, unless otherwise indicated, conventional methods of synthetic organic chemistry, protein chemistry and biochemistry and agriculture are within the skill of the art. Such techniques are explained fully in the literature. See, e.g. T. E. Creighton, *Proteins: Structures and Molecular Properties* (W. H. Freeman and Company, 1993); A. L. Lehninger, *Biochemistry* (Worth Publishers, Inc., current addition); *Methods In Enzymology* (S. Colowick and N. Kaplan eds., Academic Press, Inc.); *Remington's Agricultural Sciences*, 18th Edition (Easton, Pa.: Mack Publishing Company, 1990); Carey and Sundberg *Advanced Organic Chemistry* $3^{rd}$ Ed. (Plenum Press) Vols A and B (1992), and Organic Reactions, Volumes 1-40 (John Wiley, and Sons, 1991).

The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying FIGURES. Such modifications fall within the scope of the appended claims.

In the examples below, the following abbreviations have the following meanings. +If an abbreviation is not defined, it has its generally accepted meaning.

aq.=aqueous
LC-MS=liquid chromatography-mass spectrometry
MS=mass spectrometry
THF=tetrahydrofuran
NaHCO$_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trIzolo[4,5-b]pyridinium 3-oxid hexafluorophosphate
r. t.=room temperature
LAH=lithium aluminum hydride
DCM=dichloromethane
DMF=dimethylformamide
DMSO=dimethyl sulfoxide equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
TLC=thin layer chromatography
UV=ultraviolet
wt %=weight percent
μM=micromolar

5.1. Example 1: Synthesis

General Experimental Details

Final compounds were confirmed by HPLC/MS analysis and determined to be ≥90%. $^1H$ and $^{13}C$ NMR spectra were recorded in $CDCl_3$ (residual internal standard $CHCl_3$=δ 7.26), DMSO-$d_6$ (residual internal standard $CD_3SOCD_2H$=δ 2.50), methanol-$d_4$ (residual internal standard $CD_2HOD$=δ 3.20), or acetone-$d_6$ (residual internal standard $CD_3COCD_2H$=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium or high pressure liquid chromatography (MPLC or HPLC) was performed with silica gel columns in both the normal phase and reverse phase.

Old Synthesis

The mixed anhydride of Boc-alanine is formed by treatment with an acid chloride, in this particular example, pivaloyl chloride. The diol 3 then reacts to form XDAS in 88-91% in pot yield. During this process, up to 10% racemization is observed.

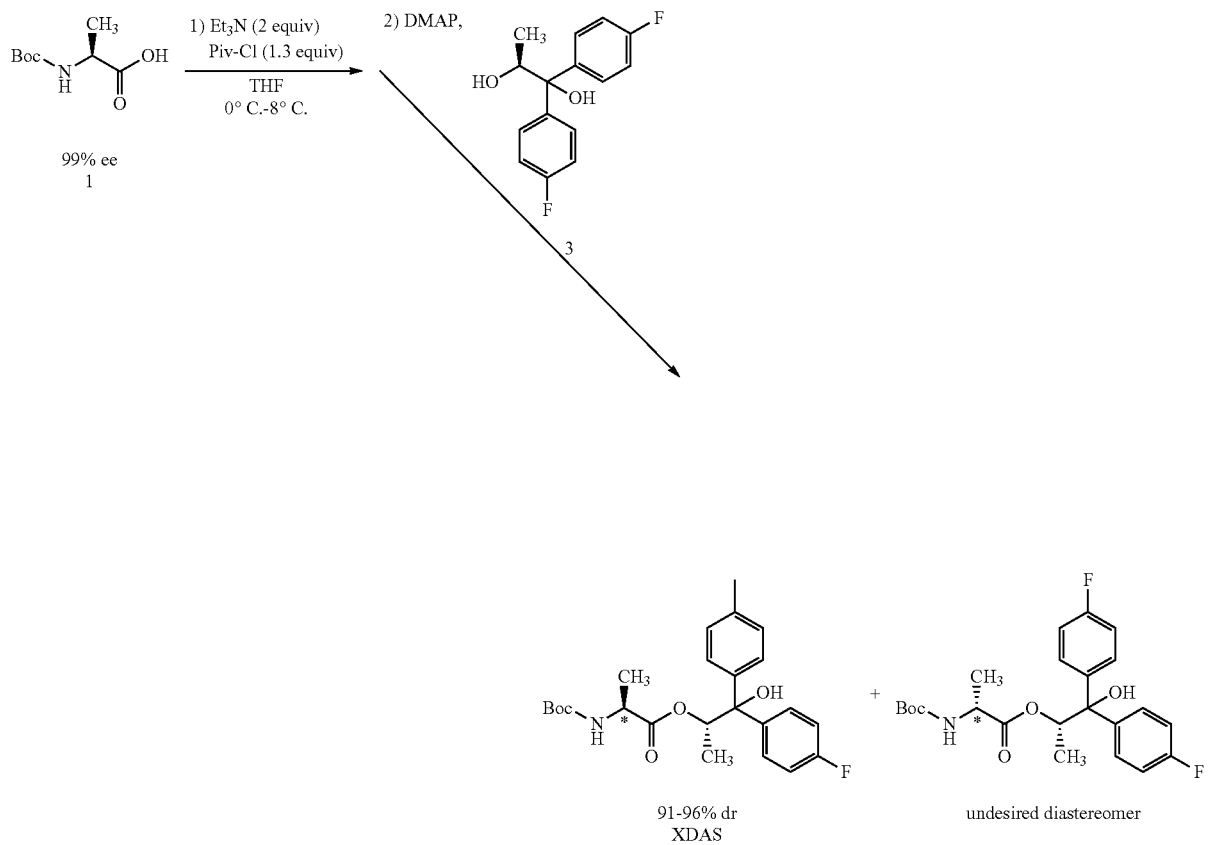

New Synthesis

The synthetic route to access XDAS has been developed and is shown in Scheme 1. In this new process Boc-alanine is reacted with diol 3 in the presence of pivalic anhydride 2, and N-methyl imidazole to form XDAS in excellent yield in pot yield of 96.9%, 99% ee and excellent in pot diastereoselectivity of >99.0% de.

Scheme 1. A new process for the preparation of XDAS using pivalic anhydride as the coupling reagent

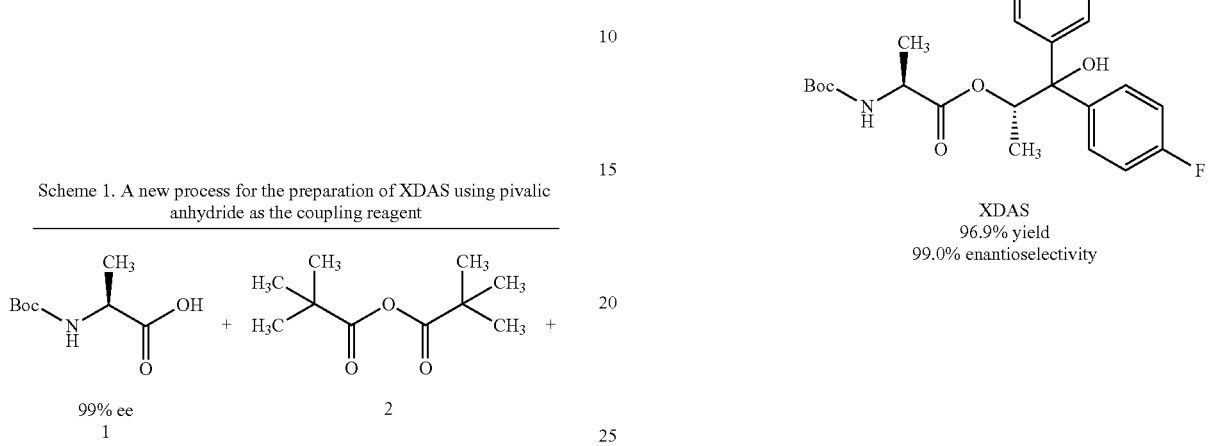

XDAS
96.9% yield
99.0% enantioselectivity

Experimental Procedure

In a 125 mL 4 neck round bottom flask was added diol (3.50 g, 3.36 g active, 12.7 mmol), Boc-alanine (3.01 g, 15.89 mmol), heptanes (35 g), 1-methylimidazole (53 µL, 54 mg, 0.66 mmol, 5 mol %), and pivalic anhydride (3.85 mL, 3.54 g, 19 mmol). The suspension was heated to 65° C. and sampling at the 5 h mark confirmed the reaction had gone to full conversion. The reaction was allowed to cool to ambient temperature and THF (30 mL) was added. The homogeneous solution was cooled to 0° C. and $H_2O$ (20 mL) added. The layers were separated and the aqueous layer was extracted with EtOAc (2×20 mL). The combined organics were washed with $K_2CO_3$ (2.52 g) dissolved in $H_2O$ (24 g), brine (1×20 mL). The total organics weighed (92.11 g). A triplicate in-pot assay, using an external method, gave a product yield of 5.36 g (96.9%). The material was used as is.

Additional reaction runs

| Run number | solvent | catalyst | equiv Boc-Ala-OH | equiv Piv₂O | isolated yield | isolated de | crude yield | crude de |
|---|---|---|---|---|---|---|---|---|
| 002 | heptanes | 4% DMAP | 1.4 | 1.6 | 68% | 99.3% | | |
| 021 | heptanes | 5% NMI | 1.4 | 1.5 | 78% | 99.1% | | |
| 017 | heptanes | 5% NMI | 1.1 | 1.25 | 92% | 99.0% | | |
| 015 | heptanes | 5% NMI | 1.1 | 1.3 | 78% | 99.0% | | |
| 012 | heptanes | 5% NMI | 1.2 | 1.2 | 79% | 99.0% | | |
| 009 | heptanes | 7% NMI | 1.3 | 1.5 | 85% | 99.6% | | |
| 022 | DCM | 5% NMI | 1.1 | 1.3 | x | x | 97% | 98.3% |

XDAS NMR characterization data: 1H NMR (400 MHz, CDCl$_3$-d) δ 7.47-7.39 (m, 2H), 7.39-7.30 (m, 2H), 6.99-6.86 (m, 4H), 5.87 (q, J=6.3 Hz, 1H), 5.12 (br d, J=8.0 Hz, 1H), 4.15-4.00 (m, 1H), 3.67 (br s, 1H), 1.35 (s, 9H), 1.14 (d, J=6.3 Hz, 3H), 0.86 (d, J=7.2 Hz, 3H).

While some embodiments have been illustrated and described, a person with ordinary skill in the art, after reading the foregoing specification, can effect changes, substitutions of equivalents and other types of alterations to the compounds of the present technology or salts, agricultural compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

We claim:

1. A process to make a compound of formula I:

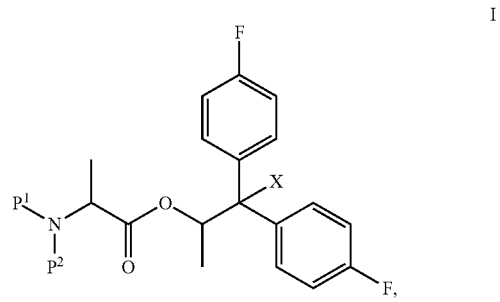

the process comprising: mixing the following compounds:

a) a compound of formula II:

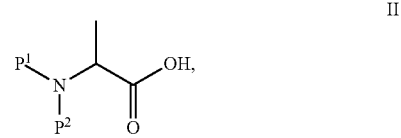

or a salt thereof;

b)

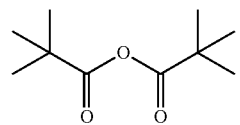

(pivalic anhydride);

c) an amine-containing acylation catalyst; and
d) a compound of formula III:

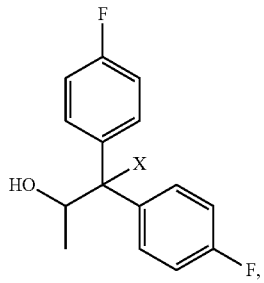

or a salt thereof; wherein
$P^2$ is hydrogen and $P^1$ is Pg, where Pg is selected from

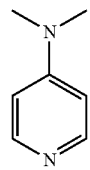

(boc or tert-butoxycarbonyl), tosyl (Ts), nosyl (Ns) and silyl; X is selected from the group consisting of: hydrogen, halogen, hydroxy, acyloxy, carboxyl ester)oxy, thiol, alkyl-thio, sulfinylamino, sulfinyloxy and sulfonyloxy.

2. The process of claim 1 wherein the acylation catalyst is

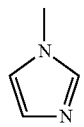

(DMAP).

3. The process of claim 1 wherein the acylation catalyst is

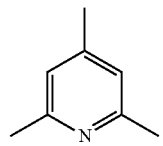

(N-methylimidazole).

4. The process of claim 1 wherein the acylation catalyst is

(pyridine).

5. The process of claim 1 wherein the acylation catalyst is (collidine).

6. The process of claim 1 wherein the amount of acylation catalyst is from 0.5-20 mol % based on the amount of compound III.

7. The process of claim 1 wherein the mixing occurs under conditions further comprising an aprotic organic solvent.

8. The process of claim 7 wherein the solvent is heptanes.

9. The process of claim 1 wherein the mixing occurs under conditions further comprising heating the mixture to about 65° C.

10. The process of claim 1 wherein compound I is

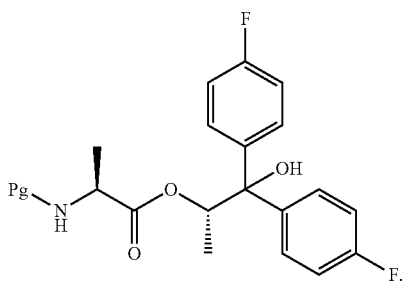

11. The process of claim 1 wherein compound I is in 99% de.

* * * * *